US009066972B2

(12) United States Patent
Dhal et al.

(10) Patent No.: US 9,066,972 B2
(45) Date of Patent: Jun. 30, 2015

(54) AMIDE DENDRIMER COMPOSITIONS

(71) Applicant: Genzyme Corporation, Cambridge, MA (US)

(72) Inventors: Pradeep K. Dhal, Westford, MA (US); David J. Harris, Lexington, MA (US); Stephen Randall Holmes-Farley, Arlington, MA (US); Chad C. Huval, Grand Coteau, LA (US); Vitaly Nivorozhkin, Boxborough, MA (US); Bruce Shutts, Bolton, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 14/260,917

(22) Filed: Apr. 24, 2014

(65) Prior Publication Data

US 2014/0235724 A1 Aug. 21, 2014

Related U.S. Application Data

(63) Continuation of application No. 13/848,968, filed on Mar. 22, 2013, now Pat. No. 8,900,560, which is a continuation of application No. 12/311,362, filed as application No. PCT/US2007/020852 on Sep. 26, 2007, now Pat. No. 8,425,887.

(60) Provisional application No. 60/847,905, filed on Sep. 29, 2006.

(51) Int. Cl.
*A61K 8/72* (2006.01)
*A61K 31/785* (2006.01)
*C07C 237/10* (2006.01)
*C08G 83/00* (2006.01)
*C08L 101/00* (2006.01)

(52) U.S. Cl.
CPC ............ *A61K 31/785* (2013.01); *C08G 83/003* (2013.01); *A61K 8/72* (2013.01); *C08L 101/00* (2013.01); *C07C 237/10* (2013.01)

(58) Field of Classification Search
None
See application file for complete search history.

(56) References Cited

U.S. PATENT DOCUMENTS

| | | |
|---|---|---|
| 3,332,841 A | 7/1967 | Ainsworth et al. |
| 3,383,236 A | 5/1968 | Brindamour |
| 3,431,138 A | 3/1969 | Zingerman et al. |
| 3,539,380 A | 11/1970 | Johnson et al. |
| 3,929,731 A | 12/1975 | Volkova et al. |
| 4,115,537 A | 9/1978 | Driscoll et al. |
| 4,211,763 A | 7/1980 | Marshall et al. |
| 4,264,573 A | 4/1981 | Powell et al. |
| 4,302,440 A | 11/1981 | John et al. |
| 4,341,563 A | 7/1982 | Kurihara et al. |
| 4,507,466 A | 3/1985 | Tomalia et al. |
| 4,539,198 A | 9/1985 | Powell et al. |
| 4,543,370 A | 9/1985 | Porter et al. |
| 4,605,701 A | 8/1986 | Harada et al. |
| 4,631,305 A | 12/1986 | Guyer et al. |
| 4,762,524 A | 8/1988 | Chambers et al. |
| 4,849,227 A | 7/1989 | Cho |
| 4,871,779 A | 10/1989 | Killat et al. |
| 4,956,182 A | 9/1990 | Bequette et al. |
| 4,983,398 A | 1/1991 | Gaylord et al. |
| 4,983,399 A | 1/1991 | Maish |
| 5,073,380 A | 12/1991 | Babu et al. |
| 5,194,464 A | 3/1993 | Itoh et al. |
| 5,262,167 A | 11/1993 | Vegesna et al. |
| 5,373,052 A | 12/1994 | Fukuda et al. |
| 5,374,422 A | 12/1994 | St. Pierre et al. |
| 5,401,515 A | 3/1995 | Woodard et al. |
| 5,414,068 A | 5/1995 | Bliem et al. |
| 5,430,110 A | 7/1995 | Ahlers et al. |
| 5,447,726 A | 9/1995 | Nomura |
| 5,455,047 A | 10/1995 | Bequette et al. |
| 5,462,730 A | 10/1995 | McTaggart et al. |
| 5,487,888 A | 1/1996 | Mandeville, et al. |
| 5,496,545 A | 3/1996 | Holmes-Farley et al. |
| 5,520,932 A | 5/1996 | McCurdy et al. |
| 5,530,092 A | 6/1996 | Meijer et al. |
| 5,561,214 A | 10/1996 | Yeske et al. |
| 5,607,669 A | 3/1997 | Mandeville, et al. |
| 5,610,268 A | 3/1997 | Meijer et al. |
| 5,618,530 A | 4/1997 | Mandeville, et al. |
| 5,624,963 A | 4/1997 | Mandeville et al. |
| 5,654,003 A | 8/1997 | Fuisz et al. |
| 5,667,775 A | 9/1997 | Holmes-Farley et al. |
| 5,679,717 A | 10/1997 | Mandeville et al. |
| 5,686,106 A | 11/1997 | Kelm et al. |

(Continued)

FOREIGN PATENT DOCUMENTS

| | | |
|---|---|---|
| CH | 656535 A5 | 7/1986 |
| EP | 0997148 | 5/2000 |

(Continued)

OTHER PUBLICATIONS

International Search Report dated Oct. 1, 2008 for PCT/US2007/020852.
Jayamurugan, Govindasamy, et al, "Synthesis of Large Generatoin Poly(Propul Ether Imine) (PETIM) Dendrimers" Tetrahedron, 82, (2006), 9582-9588.
Xiuru Li, et al., Synthesis and Charactenzation of Hyperbranched Poly(Ester Amide)s from Commercially Available Dicarboxylic Acids and Multihydroxyl Primary Amines Macromolecules, 39 (2006) 7889-7899.

(Continued)

*Primary Examiner* — James Rogers
(74) *Attorney, Agent, or Firm* — Chandra Adams

(57) ABSTRACT

Amide compounds, amide polymers, compositions including amide compounds and amide polymers may be used to bind target ions, such as phosphorous-containing compounds in the gastrointestinal tract of animals. In some cases, amide compounds and amide polymers may include a core derived from an amide polyol and an organic polyacid or ester.

3 Claims, No Drawings

(56) References Cited

U.S. PATENT DOCUMENTS

| | | |
|---|---|---|
| 5,693,675 A | 12/1997 | Mandeville et al. |
| 5,702,696 A | 12/1997 | Mandeville et al. |
| 5,703,188 A | 12/1997 | Mandeville et al. |
| 5,709,880 A | 1/1998 | Del Corral et al. |
| 5,718,920 A | 2/1998 | Notenbomer et al. |
| 5,747,067 A | 5/1998 | Auguello et al. |
| 5,750,148 A | 5/1998 | Maruyama et al. |
| 5,807,582 A | 9/1998 | Cha |
| 5,814,336 A | 9/1998 | Kelm et al. |
| 5,840,339 A | 11/1998 | Kunin |
| 5,840,766 A | 11/1998 | Mandeville et al. |
| 5,900,475 A | 5/1999 | Mandeville et al. |
| 5,919,832 A | 7/1999 | Mandeville et al. |
| 5,959,069 A | 9/1999 | Gluck et al. |
| 5,969,090 A | 10/1999 | Mandeville et al. |
| 5,985,938 A | 11/1999 | Holmes-Farley et al. |
| 6,022,533 A | 2/2000 | Goto et al. |
| 6,034,129 A | 3/2000 | Mandeville et al. |
| 6,037,444 A | 3/2000 | Rannard et al. |
| 6,083,495 A | 7/2000 | Holmes-Farley et al. |
| 6,083,497 A | 7/2000 | Huval et al. |
| 6,090,411 A | 7/2000 | Pillay et al. |
| 6,177,478 B1 | 1/2001 | Holmes-Farley et al. |
| 6,180,754 B1 | 1/2001 | Stutts et al. |
| 6,187,897 B1 | 2/2001 | Kawashima et al. |
| 6,190,650 B1 | 2/2001 | Mathews et al. |
| 6,203,785 B1 | 3/2001 | Holmes-Farley et al. |
| 6,248,318 B1 | 6/2001 | Huval et al. |
| 6,264,937 B1 | 7/2001 | Mandeville et al. |
| 6,281,252 B1 | 8/2001 | Holmes-Farley et al. |
| 6,284,275 B1 | 9/2001 | Chen |
| 6,362,266 B1 | 3/2002 | Buchholz et al. |
| 6,383,518 B1 | 5/2002 | Matsuda et al. |
| 6,423,754 B1 | 7/2002 | Holmes-Farley et al. |
| 6,509,013 B1 | 1/2003 | Holmes-Farley et al. |
| 6,534,600 B2 | 3/2003 | Dvornic et al. |
| 6,566,407 B2 | 5/2003 | Holmes-Farley et al. |
| 6,600,011 B2 | 7/2003 | McDonnell et al. |
| 6,605,270 B1 | 8/2003 | Mandeville et al. |
| 6,696,087 B2 | 2/2004 | Matsuda et al. |
| 6,726,905 B1 | 4/2004 | Mandeville et al. |
| 6,733,780 B1 | 5/2004 | Tyler et al. |
| 6,844,372 B2 | 1/2005 | Goto et al. |
| 6,858,203 B2 | 2/2005 | Holmes-Farley et al. |
| 6,908,609 B2 | 6/2005 | Simon et al. |
| 7,014,846 B2 | 3/2006 | Holmes-Farley et al. |
| 7,019,085 B2 | 3/2006 | Albright |
| 7,081,509 B2 | 7/2006 | Wagner et al. |
| 7,087,223 B2 | 8/2006 | Goto et al. |
| 7,101,960 B2 | 9/2006 | Mandeville et al. |
| 7,220,406 B2 | 5/2007 | Burke |
| 7,335,795 B2 | 2/2008 | Chang et al. |
| 7,342,083 B2 | 3/2008 | Chang et al. |
| 7,385,012 B2 | 6/2008 | Chang et al. |
| 7,449,605 B2 | 11/2008 | Chang et al. |
| 7,459,151 B2 | 12/2008 | Holmes-Farley et al. |
| 7,459,502 B2 | 12/2008 | Connor et al. |
| 7,589,238 B2 | 9/2009 | Connor et al. |
| 2002/0054903 A1 | 5/2002 | Tyler et al. |
| 2002/0114774 A1 | 8/2002 | Fitzpatrick et al. |
| 2002/0122786 A1 | 9/2002 | Matsuda et al. |
| 2002/0159968 A1 | 10/2002 | Petersen et al. |
| 2002/0160050 A1 | 10/2002 | Elema et al. |
| 2002/0168333 A1 | 11/2002 | Burke |
| 2002/0182168 A1 | 12/2002 | Holmes-Farley et al. |
| 2002/0187120 A1 | 12/2002 | Holmes-Farley et al. |
| 2002/0187121 A1 | 12/2002 | Burke |
| 2003/0039627 A1 | 2/2003 | Holmes-Farley et al. |
| 2003/0049226 A1 | 3/2003 | Burke et al. |
| 2003/0086898 A1 | 5/2003 | Holmes-Farley et al. |
| 2003/0133902 A1 | 7/2003 | Holmes-Farley et al. |
| 2003/0175349 A1 | 9/2003 | Garg et al. |
| 2003/0180250 A1 | 9/2003 | Chauhan et al. |
| 2003/0199090 A1 | 10/2003 | Monahan et al. |
| 2004/0022844 A1 | 2/2004 | Hasenzahl et al. |
| 2004/0170695 A1 | 9/2004 | Elama et al. |
| 2004/0185111 A1 | 9/2004 | Rubino et al. |
| 2004/0191209 A1 | 9/2004 | Oba |
| 2004/0191212 A1 | 9/2004 | Holmes-Farley et al. |
| 2005/0084476 A1 | 4/2005 | Goto et al. |
| 2005/0096438 A1 | 5/2005 | Chang et al. |
| 2005/0123614 A1 | 6/2005 | Kim et al. |
| 2005/0131138 A1 | 6/2005 | Connor et al. |
| 2005/0131161 A1 | 6/2005 | Mandeville et al. |
| 2005/0147580 A1 | 7/2005 | Connor et al. |
| 2005/0165190 A1 | 7/2005 | Chang et al. |
| 2005/0208095 A1 | 9/2005 | Hunter et al. |
| 2005/0209423 A1 | 9/2005 | Chang et al. |
| 2005/0220752 A1 | 10/2005 | Charmot et al. |
| 2005/0220889 A1 | 10/2005 | Charmot et al. |
| 2005/0220890 A1 | 10/2005 | Charmot et al. |
| 2005/0239901 A1 | 10/2005 | Chang et al. |
| 2005/0260236 A1 | 11/2005 | Tyler et al. |
| 2005/0282010 A1 | 12/2005 | Xu |
| 2006/0024336 A1 | 2/2006 | Charmot et al. |
| 2006/0029663 A1 | 2/2006 | Uchida et al. |
| 2006/0034914 A1 | 2/2006 | Tyler et al. |
| 2006/0043984 A1 | 3/2006 | Miller et al. |
| 2006/0047086 A1 | 3/2006 | Albright et al. |
| 2006/0054914 A1 | 3/2006 | Hsian Yi |
| 2006/0088592 A1 | 4/2006 | Choi et al. |
| 2006/0134225 A1 | 6/2006 | Moerck et al. |
| 2006/0171916 A1 | 8/2006 | Holmes-Farley et al. |
| 2006/0177415 A1 | 8/2006 | Burke |
| 2006/0239959 A1 | 10/2006 | Holmes-Farley et al. |
| 2006/0251614 A1 | 11/2006 | Bhagat et al. |
| 2006/0258812 A1 | 11/2006 | Gopalkrishna et al. |
| 2006/0292192 A1 | 12/2006 | Hasenzahl et al. |
| 2007/0035313 A1 | 2/2007 | Wuersch et al. |
| 2007/0059277 A1 | 3/2007 | Bhagat et al. |
| 2007/0071715 A1 | 3/2007 | DeLuca et al. |
| 2007/0094779 A1 | 5/2007 | Dauphin |
| 2007/0098678 A1 | 5/2007 | Bhagat et al. |
| 2007/0110707 A1 | 5/2007 | Ravi |
| 2007/0155950 A1 | 7/2007 | Mandeville et al. |
| 2007/0224283 A1 | 9/2007 | Chang et al. |
| 2008/0107737 A1 | 5/2008 | Chang et al. |
| 2008/0226735 A1 | 9/2008 | Moerck et al. |
| 2008/0292697 A1 | 11/2008 | Tyler et al. |

FOREIGN PATENT DOCUMENTS

| | | |
|---|---|---|
| EP | 1153940 | 11/2001 |
| EP | 1682606 | 7/2006 |
| EP | 1687349 | 8/2006 |
| EP | 1742613 | 1/2007 |
| EP | 0211991 | 3/2007 |
| EP | 1831266 | 9/2007 |
| JP | 60152424 | 8/1985 |
| JP | 10316576 | 12/1998 |
| JP | 200178182 | 6/2000 |
| WO | WO 93/00915 | 1/1993 |
| WO | WO 94/19379 | 9/1994 |
| WO | WO 95/05184 | 2/1995 |
| WO | WO 96/39156 | 12/1996 |
| WO | WO 98/29107 | 7/1998 |
| WO | WO 98/42355 | 10/1998 |
| WO | WO 98/44933 | 10/1998 |
| WO | WO 99/22721 | 5/1999 |
| WO | WO 99/22743 | 5/1999 |
| WO | WO 00/22008 | 4/2000 |
| WO | WO 01/28527 | 4/2001 |
| WO | WO 2004/037274 | 5/2004 |
| WO | WO 2004/099288 | 11/2004 |
| WO | WO 2005/041900 | 5/2005 |
| WO | WO 2005/041902 | 5/2005 |
| WO | WO 2005/092039 | 10/2005 |
| WO | WO 2006/043984 | 4/2006 |
| WO | WO 2006/050314 | 5/2006 |

OTHER PUBLICATIONS

Perignon, Nelly et al., "Formation and Stabilization in Water of Metal Nanoparticles by a Hyperbranched Polymer Chemically Analgous to PAMAM Dendrimers" Chem Mater., 16 (2004)4856-4858.

(56) References Cited

OTHER PUBLICATIONS

Koc, Fikret, et al, "Highly Regioselective Synthesis pf Amino-Functionalized Dendritic PolyGlycerols by a One Pot Hydroformylation/Reductive Amination Sequence" J. Org. Chem., 70 (2005) 2021-2025.

Gao, Chao, "Hyperbranched Copolymers Made from A2, B2 and BB'2 Type Monomers, 3a: Comparison of Copoly(Sulfone-Amine)s Containing Piperazine and 4,4'-Trimethyienedipiperidine Untis" Macromolecular Chemistry and Physics, (2001), 202(15), 3035-3042.

Gao, Chao, Hyperbranched Polymers made from A2- and BB2'-type Monomers: 3. Polyaddition of N-Methyl 1,3-Propanediamine to Divinyl Sulfone: Macromolecular Chemistry and Physics, (2001), 202(12), 2623-2629.

Gao, Chao, "Hyperbranched Copolymers Made from A2, B2 and BB'2 Type Monomers (iv), Copolymerization of Divinyl Sulfone with 4,4'-trimethylenodipiperidine and N-Ethylethylenediamine" Science in China. Series B: Chemistry, (2001), 44(2), 207-215

Gao, C., "Preparation of Water Soluble Hyperbranched Poly(Sulfone-Amine)s by Polyaddition of N-Ethylethylenediamine to Divinyl Sulfone" Polymer, (2001), 42(18), 7603-7810.

Gao, C, "Hyperbranched Polymers Made from A2, B2 and BB'2 Type Monomers, 2. Preparation of Hyperbranched Copoly(Sulfone-Amine)s by Polyaddition of N-ethylethylenediamine and Piperazine to Divinylsulfone" Polymer, (2001). 42(8), 3437-3443.

Gao, Chao, "Synthesis of Hyperbranched Polymers from Commercially Available A2 and BB'2 Type Monomers" Chemical Communications (Cambridge): 1, (2001), 107-108.

Geo, Chao, "Polyaddition of B2 and BB'2 Type Monomers to A2 Type Monomer. 1. Synthesis of Highly Branched Copoly(Sulfon-Amine)s" Macromolecules, (2001), 34(2), 156-161.

Yan, Deyue, "Hyperbranched Polymers Made from A2 and BB'2 Type Monomers, 1. Polyaddition of 1-(2-Aminoethyl)Piperazine to Divinyl Sulfone," Macromolecules, (2000), 33(21), 7693-7699.

Hobson, Lois J., et al., "Poly(Amidoamine) Hyperbranched Systems: Synthesis, Structure and Characterization" Polymer. 40, (1999), 1279-129.

Rosenbaum, Holmes-Farley: Mandevillie, Pitruzzello, Goldberg, "Effect of RenaGelm, a Non-Absorbable, Cross-Linked; Polymeric Phosphate Binder, on Urinary Phosphorus Excretion in Rats" Nephrology Dialysis Transplantation, vol. 12. (1997), 961-964.

Mourey, T.H., et al., "Unique Behavior of Dendrilic Molecules Intrinsic Viscosity of Polyether Dendrimers" Macromolecules, 25, (1992), 2401-2406.

Janssen, H.M., et al., "The Synthesis and Characterization of Dendritic Molecules" Eindhoven University of Technology, (No Date Available).

Klapper, Marcus, et al., "Poly(Methylene Amine): A Polymer with the Maximum Possible Number of Amino Groups on a Polymer Backbone" Angew. Chem. Int. Ed., 42, (2003), 4687-4690 (XP002456407).

Kuga, Shigenori, "Pore Size Distribution Analysis of Gel Substances by Size Exclusion Chromatography", J. Chromatography, 206, (1961), 449-461.

Kremer, Michael, et al., "Pore-Size Distributions of Cationic Polyacrylamide Hydrogels Varying in Initial Monomer Concentration and Crosslnker/Monomer Ratio" Macromolecules, 27, (1994), 2065-2973.

Jansen. Johan F.G.A., et al., "The Dendritic Box: Shape-Selective Liberation of Encapsulated Guests" J. Am. Chem, Soc., 117, (1995),4417-4418.

de Brabancter-van den Berg, Ellen M. M., et al., "Poly(Propylenimin)-Dendrimere Synthese in groBerem MaBstab durch heterogen katalysierte Hydrierungan" Angew. Chem., (1993), 1370-1372. (In Geman Only).

Duncan, Ruth, et al., "Dendrimer Biocompatibility and Toxicity" Advanced Drug Delivery Reviews, 57 (2005), 2215-223).

Huval, Chad C., et al., "Syntheses of Hydrophobically Modified Cationic Hydrogels by Copolymerization of Alkyl Substituted Dratlylamine Monomers and Their Use as Bile Acid Sequestrants" European Polymer Journal, 40, (2004), 693-701.

Newkome, George R., et al., "Improved Synthesis of an Ethereal Tetraamine Core for Dendrimer Construction" J. Org. Chem., 67. (2002), 3957-3960.

Schatzlein Andreas G. et al., "Preferential Liver Gene Expression With Polypropylenimine Dendrimers" Journal of Controlled Release, 101, (2005), 247-258.

Shea, Lu, et al., "Transport Properties of Cross-Linked Polyimide Membranes Induced by Different Generations of Diaminobutane (DAB) Dendrimers" Journal of Membrane Science. 238, (2004), 153-163.

Stasko, Nathan A., et al., "Dendrimers as a Scaffold for Nitric Oxide Release" J. Am. Chem. Soc., 128, (2006), 8265-8271

Xiao, Youchang, et al., "Effects of Thermal Treatments and Dendrimers Chemical Structures on the Properties of Highly Surface Cross-Linked Polyimide Filmes" Ind. Eng. Chem. Res., 44, (2005), 3059-3067.

Bhadra, D., et al., "Giycodendrimeric Nanoparticulate Carriers of Primaquine Phosphate for Liver Targeting" International Journal of Pharmaceutics, 295, (Mar. 2005), 221-233.

Pavlov, G. M., et al., "Molecular Characteristics of Poly(Propylene Imine)Deridrimers as Studied With Translational Diffusion and Viscometry" Colloid. Polym. Sci., 280, (2002), 416-423.

Chertow: Glenn M., et al., "The Effects of Sevelamer and Calcium Acetate on Proxies of Atherosclerotic and Arteriosclerotic Vascular Disease in Hemodialysis Patients", Am. J. Nephrol., 235, (2003), 307-314.

Katopodis, K. P., et al., "Effectiveness of Aluminum Hydroxide Timing Administration in Relation to Meals in Controlling Hyperphosphatemia in Dialysis Patients" The international Journal of Artificiai Organs. 28:8, (2005), 803-807.

Selmeczi, B., et al., "Investigations of the influence of some Novel Auxiliary Agents on the Physical Properties of Tablets" Pharmaceutical Technological Institute of the Medical University of Szeged (Hungary), (No date available).

Mattsson. S., et al., "Formulation of High Tensile Strength Rapidly Disintegrating Tablets Evaluation of the Effect of Some Binder Properties" S.T.P Pharma Sciences, 11:3. (2001), 211-220.

Soltero, Richard, et al., "The Effects of PH. Ionic Concentration and Ionic Species of Dissolution Media on the Release Rates of Quinidine Gluconate Sustained Release Dosage Forms" Drug Development and Industrial Pharmacy, 17:1. (1991), 113-140.

Hammouda. Y., et al., "The Use of Sodium Chloride as a Directly Compressible Filler in Therapeutic Tablets" Pharm. Ind., 37:5, (1976), 361-363.

Caramella, Carla, et al., "Experimental Evidence of Disintegration Mechanisms". Acta Pharma. Technol. 35:1, (1989), 30-33.

Tirkkonen, Sirpa, et al., "Enhancement of Drug Release from Ethylcellulose Microcapsules Using Solid Sodium Chloride in the Wall", International Journal of Pharmaceutics, 86, (1992), 39-51.

Mitchell, Karen, et al., "The Influence of Additives on the Cloud Point, Disintegration and Dissolution of Hydoxypropylmethylcalluiose Gels and Matrix Tablets" International Journal of Pharmaceutics. 66, (1990) 233-242.

Tirkkonen, Sirpa, et al., "Release of Indomethacin from Tabletted Ethylcellulose Microcapsules" International Journal of Pharmaceutics, 92, (1993), 55-62.

Ferrari, F., et al., "Investigation on Bonding and Disintegration Properties of Pharmaceutical Materials" International Journal of Pharmaceutics, 136. (1996), 71-79.

Lin, Shan-Yang, et al., "Influence of Excipients, Drugs, and Osmotic Agent in the Inner Core on the Time-Controlled Disintegration of Compression-Coated Ethylcellulose Tablets" Journal of Pharmaceutical Sciences, 91:9, (Sep. 2002), 2040-2046.

Schutz, W., "Brief Evaluation: Sevelamer Hydrochloride" Drug, Therapy Criticism, Hans Marseille Publishers GmbH, Munich, Issue 3. (2001), 621-626.

Maroni, Bradley J., et al., "Renal Bioreplacement Therapy is Associated with a Reduction in Mortality in Patients with Acute Renal Failure: Results of a Randomized, Multi-Center, Phase II Trial" ERA-EDTA: Abstract #1551794, (2006).

"Renvela: sevelamer carbonate" Prescribing Information: Genzyme Corporation, Nov. 2007.

AMIDE DENDRIMER COMPOSITIONS

FIELD OF THE INVENTION

This invention relates to amide polymers for binding compounds or ions, and more specifically relates to pharmaceutically acceptable compositions, amide dendrimers, amide polymers or residues thereof for binding target ions.

BACKGROUND OF THE INVENTION

Hyperphosphatemia frequently accompanies diseases associated with inadequate renal function such as end stage renal disease (ESRD), hyperparathyroidism, and certain other medical conditions. The condition, especially if present over extended periods of time, leads to severe abnormalities in calcium and phosphorus metabolism and can be manifested by aberrant calcification in joints, lungs, and eyes.

Therapeutic efforts to reduce serum phosphate include dialysis, reduction in dietary phosphate, and oral administration of insoluble phosphate binders to reduce gastrointestinal absorption. Many such treatments have a variety of unwanted side effects and/or have less than optimal phosphate binding properties, including potency and efficacy. Accordingly, there is a need for compositions and treatments with good phosphate-binding properties and good side effect profiles.

BRIEF SUMMARY OF THE INVENTION

In one aspect, the present invention relates to amide compounds, amide polymers and/or compositions comprising or derived from the same or residues thereof. The amide compounds (amide dendrimers) comprise amide polyol cores (formed, for example, from an organic polyacid or ester thereof substituted at one or more of the acid hydroxyl groups with one or more amine polyols). The amide compounds can be crosslinked to form amide polymers. Compositions can comprise one or more amide compounds or residues thereof and/or amide polymers or residues thereof. Several embodiments of the invention, including this aspect of the invention, are described in further detail as follows. Generally, each of these embodiments can be used in various and specific combinations, and with other aspects and embodiments for a variety of pharmaceutical and therapeutic uses unless otherwise stated herein.

In another aspect, the present invention relates to amine polyether compounds, amine polyether polymers and/or compositions comprising or derived from the same or residues thereof. The amine polyether compounds (amine polyether dendrimers) comprise amine polyol cores. The amine polyether compounds may be crosslinked to form amine polyether polymers. Compositions can comprise one or more amine polyether compounds or residues thereof and/or amine polyether polymers or residues thereof. Several embodiments of the invention, including this aspect of the invention, are described in further detail as follows. Generally, each of these embodiments can be used in various and specific combinations, and with other aspects and embodiments for a variety of pharmaceutical and therapeutic uses unless otherwise stated herein.

In addition to the amide compounds, amide polymers, amine polyether compounds and amine polyether polymers of the present invention as described herein, other forms of the amide compounds, amide polymers, amine polyether compounds and amine polyether polymers are within the scope of the invention including pharmaceutically acceptable salts, solvates, hydrates, prodrugs, polymorphs, clathrates, and isotopic variants and mixtures thereof of the amide compounds, amide polymers, amine polyether compounds and/or amine polyether polymers.

In addition, amide compounds, amide polymers, amine polyether compounds and amine polyether polymers of the invention may have optical centers, chiral centers or double bonds and the amide compounds, amide polymers, amine polyether compounds and amine polyether polymers of the present invention include all of the isomeric forms of these compounds and polymers, including optically pure forms, racemates, diastereomers, enantiomers, tautomers and/or mixtures thereof.

In a first embodiment, the invention is, consists essentially of, or comprises an amide compound or an amide polymer that comprises at least one amide compound or residue thereof, where the amide compound is represented by Formula I, as follows:

Formula I

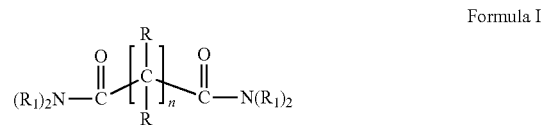

wherein n independently represents an integer from 0-20, for example, 1-15, 1-2, 3-6, 7-10, 11-15, such as 1, 2, 3, 4, 5, 6, 7, 8, 9, 10, 11, 12, 13, 14, 15, 16, 17, 18, 19 or 20; R independently represents a hydrogen radical, a hydroxyl radical, $-OR_3$, $-R_2OH$, $-R_2OR_3$, or $C(O)N(R_1)_2$; $R_1$ independently represents a hydrogen radical, a hydroxyl radical, $-OR_3$, or a branched or unbranched substituted $C_1$-$C_{10}$, such as a $C_1$, $C_2$, $C_3$, $C_4$, $C_5$, $C_6$, $C_7$, $C_8$, $C_9$, $C_{10}$, alkyl radical, wherein one or more carbon atoms of the alkyl radical may be partially or fully substituted with $-OH$ and/or $-OR_3$ groups, for example a $C_3$-$C_8$ branched alkyl radical having more than one substitution, such as $C_4$-$C_7$ branched alkyl substituted with 2 or more $-OH$ and/or $-OR_3$ groups, or $C_3$ branched alkyl substituted with 3 or more $-OH$ and/or $-OR_3$ groups; $R_2$ independently represents a substituted or unsubstituted, branched or unbranched alkyl radical; and $R_3$ independently represents the following Formula II:

Formula II

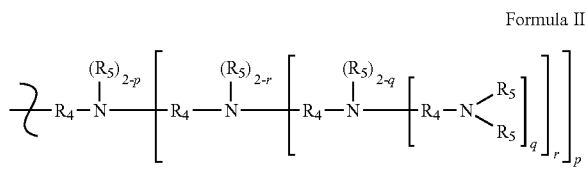

wherein p, q and r independently represent an integer from 0-2, for example, 0, 1 or 2; $R_4$ independently represents

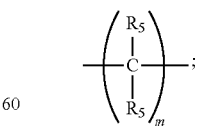

wherein m independently represents an integer from 1-20, for example, 1-15, 1-2, 3-6, 7-10, 11-15, such as 1, 2, 3, 4, 5, 6, 7, 8, 9, 10, 11, 12, 13, 14, 15, 16, 17, 18, 19 or 20; $R_5$ independently represents a hydrogen radical; a substituted or un-substituted alkyl radical; a substituted or un-substituted aryl radical; or $R_5$ and a neighboring $R_5$ together represent a link or links comprising a residue of a crosslinking agent, for example epichlorohydrin or other crosslinking agents, a substituted or un-substituted alicyclic radical, a substituted or un-substituted aromatic radical, or a substituted or un-substituted heterocyclic radical; or $R_5$ represents a link with another compound or a residue thereof.

In another aspect, the invention provides methods of treating an animal, including a human. The method generally involves administering a therapeutically effective amount of an amide polymer described herein.

Another aspect of the invention is a pharmaceutical composition comprising one or more amide polymers or amine polyether polymers of the present invention with at least one pharmaceutically acceptable carrier or excipient. The amide polymers and amine polyether polymers described herein have several therapeutic applications. For example, they are useful in removing compounds or ions such as anions, for example phosphorous-containing compounds or phosphorous containing ions such as organophosphates and/or phosphates, from the gastrointestinal tract, such as from the stomach, small intestine and/or large intestine. In some embodiments, the amide polymers and amine polyether polymers are used in the treatment of phosphate imbalance disorders and renal diseases.

In some embodiments, the invention comprises an amide polymer or an amine polyether polymer that comprises an amide dendrimer or residue thereof or an amine polyether dendrimer or residue thereof, where the dendrimer comprises an amide polyol core or an amine polyol core and branches emanating from the core, where the branches are based on substituted or un-substituted α, β unsaturated nitrile units. The branches may be formed using a reiterative reaction sequence that includes a Michael addition of the substituted or un-substituted α, β unsaturated nitrile and a reduction of the nitrile group to a primary amine.

In yet another aspect, the amide polymers, amine polyether polymers and/or pharmaceutical compositions are useful for removing other solutes, such as chloride, bicarbonate, and/or oxalate containing compounds or ions. Amide polymers and amine polyether polymers removing oxalate compounds or ions find use in the treatment of oxalate imbalance disorders. Amide polymers and amine polyether polymers removing chloride compounds or ions find use in treating acidosis, for example. In some embodiments, the amide polymers and amine polyether polymers are useful for removing bile acids and related compounds.

The invention further provides compositions containing any of the above amide polymers or amine polyether polymers where the amide polymer or amine polyether polymers is in the form of particles and where the particles are encased in one or more shells.

In another aspect, the invention provides pharmaceutical compositions. In some embodiments, the pharmaceutical composition contains an amide polymer or an amine polyether polymers of the invention and a pharmaceutically acceptable excipient. In some embodiments, the composition is a liquid formulation in which the amide polymer or the amine polyether polymer is dispersed in a liquid vehicle, such as water, and suitable excipients. In some embodiments, the invention provides a pharmaceutical composition comprising an amide polymer or an amine polyether polymer for binding a target compound or ion, and one or more suitable pharmaceutical excipients, where the composition is in the form of a tablet, sachet, slurry, food formulation, troche, capsule, elixir, suspension, syrup, wafer, chewing gum or lozenge. In some embodiments the composition contains a pharmaceutical excipient selected from the group consisting of sucrose, mannitol, xylitol, maltodextrin, fructose, sorbitol, and combinations thereof. In some embodiments the target anion of the amide polymer is an organophosphate and/or phosphate. In some embodiments the amide polymer is more than about 50% of the weight of the tablet. In some embodiments, the tablet is of cylindrical shape with a diameter of from about 12 mm to about 28 mm and a height of from about 1 mm to about 8 mm and the amide polymer comprises more than 0.6 to about 2.0 gm of the total weight of the tablet.

In some of the compositions of the invention, the excipients are chosen from the group consisting of sweetening agents, binders, lubricants, and disintegrants. Optionally, the amide polymer is present as particles of less than about 80 μm mean diameter. In some of these embodiments, the sweetening agent is selected from the group consisting of sucrose, mannitol, xylitol, maltodextrin, fructose, and sorbitol, and combinations thereof.

In some embodiments, the invention provides amide polymers or compositions that comprise an amide dendrimer or residue thereof, where the amide dendrimer is formed from a core that comprises an amide polyol that is substituted with one or more amine groups represented by the following Formula II:

Formula II

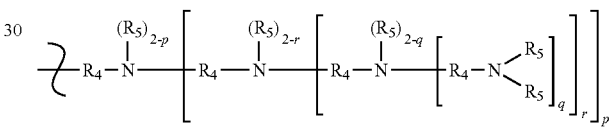

wherein p, q and r independently represent an integer from 0-2, for example, 0, 1 or 2; $R_4$ independently represents

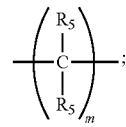

wherein m independently represents an integer from 1-20, for example, 1-15, 1-2, 3-6, 7-10, 11-15, such as 1, 2, 3, 4, 5, 6, 7, 8, 9, 10, 11, 12, 13, 14, 15, 16, 17, 18, 19 or 20; $R_5$ independently represents a hydrogen radical; a substituted or un-substituted alkyl radical; a substituted or un-substituted aryl radical; or $R_5$ and a neighboring $R_5$ together represent a link or links comprising a residue of a crosslinking agent, for example epichlorohydrin or other crosslinking agents, a substituted or un-substituted alicyclic radical, a substituted or un-substituted aromatic radical, or a substituted or un-substituted heterocyclic radical; or $R_5$ represents a link with another compound or a residue thereof.

In still other embodiments, a polymer network may include two or more polymers, where at least one of the polymers is an amide polymer derived from an amide compound represented by Formula I, that may be linked to form a polymer network. For example, in some embodiments a polymer network may comprise a residue of two or more amide polyols, a residue of one or more substituted or un-substituted α, β unsaturated nitrile groups and a residue of one or more crosslinking agents. In some embodiments, the polymer network may be formed where all or substantially all of the polymers may be amide polymers that are derived from amide compounds represented by Formula I.

DETAILED DESCRIPTION OF THE INVENTION

In one aspect, the present invention provides amide compounds, amide polymers, compositions and methods of using amide polymers or compositions comprising an amide polymer or amide compound or residue thereof, where the amide compound is represented by Formula I. In some embodiments, the compositions may comprise amide polymers that may be derived from two or more of the amide compounds described herein.

In addition, some embodiments may include multiple amide compounds or residues thereof or amine polyether compounds or residues thereof that repeat in a copolymer or polymer. Such polymers may include one or more additional compounds that may be included in a polymer backbone or as pendant groups either individually or as repeating groups, and that may provide separation between the individual amide polymers or amine polyether polymers.

As used herein, unless otherwise stated, the term "derived from" is understood to mean: produced or obtained from another substance by chemical reaction, especially directly derived from the reactants, for example an amide compound may be derived from the reaction of an amide polyol and a substituted or un-substituted α, β unsaturated nitrile that is subsequently hydrogenated to form an amide compound having one or more generations of dendritic branching. Additionally, an amide compound that is reacted with a linking agent, such as a crosslinking agent results in an amide polymer that is derived from the amide compound and the linking agent.

In some embodiments, the present invention is an amide compound, an amide polymer (comprising or derived from said amide compound or a residue thereof), a pharmaceutical composition (comprising or derived from said amide compound or a residue thereof or comprising or derived from said amide polymer or a residue thereof) or a method of using the same in a therapeutically effective amount to remove a compound or ion, such as a phosphorous-containing compound or a phosphorous-containing ion (e.g. phosphate), from the gastrointestinal tract of an animal where the amide compound is represented by Formula I, as follows:

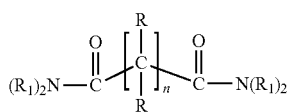

Formula I wherein n independently represents an integer from 0-20, for example, 1-15, 1-2, 3-6, 7-10, 11-15, such as 1, 2, 3, 4, 5, 6, 7, 8, 9, 10, 11, 12, 13, 14, 15, 16, 17, 18, 19 or 20; R independently represents a hydrogen radical, a hydroxyl radical, $-OR_3$, $-R_2OH$, $-R_2OR_3$, or $C(O)N(R_1)_2$; $R_1$ independently represents a hydrogen radical, a hydroxyl radical, $-OR_3$, or a branched or unbranched substituted $C_1$-$C_{10}$, such as a $C_1$, $C_2$, $C_3$, $C_4$, $C_5$, $C_6$, $C_7$, $C_8$, $C_9$, $C_{10}$, alkyl radical, wherein one or more carbon atoms of the alkyl radical may be partially or fully substituted with —OH and/or $-OR_3$ groups, for example a $C_3$-$C_8$ branched alkyl radical having more than one substitution, such as $C_4$-$C_7$ branched alkyl substituted with 2 or more —OH and/or $-OR_3$ groups, or $C_3$ branched alkyl substituted with 3 or more —OH and/or —$OR_3$ groups; $R_2$ independently represents a substituted or unsubstituted, branched or unbranched alkyl radical; and $R_3$ is independently represented by the following Formula II:

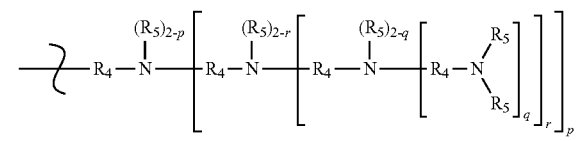

Formula II wherein p, q and r independently represent an integer from 0-2, such as 0, 1 or 2; $R_4$ independently represents

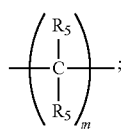

wherein m independently represents an integer from 1-20, for example, 1-15, 1-2, 3-6, 7-10, 11-15, such as 1, 2, 3, 4, 5, 6, 7, 8, 9, 10, 11, 12, 13, 14, 15, 16, 17, 18, 19 or 20; $R_5$ independently represents a hydrogen radical; a substituted or un-substituted alkyl radical; a substituted or un-substituted aryl radical; or $R_5$ and a neighboring $R_5$ together represent a link or links comprising a residue of a crosslinking agent, for example epichlorohydrin or other crosslinking agents, a substituted or un-substituted alicyclic radical, a substituted or un-substituted aromatic radical, or a substituted or un-substituted heterocyclic radical; or $R_5$ represents a link with another compound or a residue thereof.

In some embodiments, the present invention is an amide compound, an amide polymer (comprising or derived from said amide compound or a residue thereof), a pharmaceutical composition (comprising or derived from said amide compound or a residue thereof or comprising or derived from said amide polymer or a residue thereof) or a method of using the same in a therapeutically effective amount to remove a compound or ion, such as a phosphorous-containing compound or a phosphorous-containing ion (e.g. phosphate), from the gastrointestinal tract of an animal where the amide compound is represented by Formula I, wherein $R_1$ independently represents a branched or unbranched substituted $C_1$-$C_{10}$ alkyl radical that is partially or fully substituted with 1-20, for example 2-10, 2-6, 2-4, such as 1, 2, 3, 4, 5, 6, 7, 8, 9, 10, 11, 12, 13, 14, 15, 16, 17, 18, 19 or 20, —OH and/or $OR_3$ groups.

In some embodiments, the present invention is an amide compound, an amide polymer (comprising or derived from said amide compound or a residue thereof), a pharmaceutical composition (comprising or derived from said amide compound or a residue thereof or comprising or derived from said amide polymer or a residue thereof) or a method of using the same in a therapeutically effective amount to remove a compound or ion, such as a phosphorous-containing compound or a phosphorous-containing ion (e.g. phosphate), from the gastrointestinal tract of an animal where the amide compound is represented by Formula I, wherein at least one R comprises $-OR_3$.

In some embodiments, the present invention is an amide compound, an amide polymer (comprising or derived from said amide compound or a residue thereof), a pharmaceutical composition (comprising or derived from said amide compound or a residue thereof or comprising or derived from said amide polymer or a residue thereof) or a method of using the same in a therapeutically effective amount to remove a compound or ion, such as a phosphorous-containing compound or a phosphorous-containing ion (e.g. phosphate), from the gastrointestinal tract of an animal where the amide compound is represented by Formula I, and where $R_3$ independently represents a group represented by the following Formula IIa:

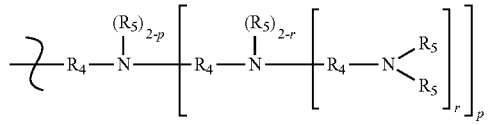

Formula IIa where p, r, $R_4$ and $R_5$ are as defined above.

In some embodiments, the present invention is an amide compound, an amide polymer (comprising or derived from said amide compound or a residue thereof), a pharmaceutical composition (comprising or derived from said amide compound or a residue thereof or comprising or derived from said amide polymer or a residue thereof) or a method of using the same in a therapeutically effective amount to remove a compound or ion, such as a phosphorous-containing compound or a phosphorous-containing ion (e.g. phosphate), from the gastrointestinal tract of an animal where the amide compound is represented by Formula I, where $R_3$ independently represents a group represented by the following Formula IIb:

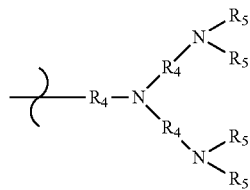

Formula IIb where $R_4$ and $R_5$ are as defined above.

In some embodiments, the present invention is an amide compound, an amide polymer (comprising or derived from said amide compound or a residue thereof), a pharmaceutical composition (comprising or derived from said amide compound or a residue thereof or comprising or derived from said amide polymer or a residue thereof) or a method of using the same in a therapeutically effective amount to remove a compound or ion, such as a phosphorous-containing compound or a phosphorous-containing ion (e.g. phosphate), from the gastrointestinal tract of an animal where the amide compound is represented by Formula III, as follows:

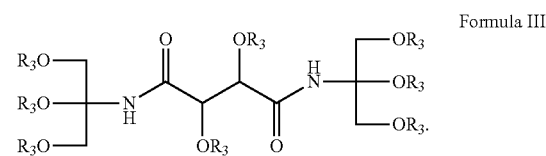

Formula III where $R_3$ independently represents a group represented by Formula II, Formula IIa, or Formula IIb as defined above.

In some embodiments, the present invention is an amide compound, an amide polymer (comprising or derived from said amide compound or a residue thereof), a pharmaceutical composition (comprising or derived from said amide compound or a residue thereof or comprising or derived from said amide polymer or a residue thereof) or a method of using the same in a therapeutically effective amount to remove a compound or ion, such as a phosphorous-containing compound or a phosphorous-containing ion (e.g. phosphate), from the gastrointestinal tract of an animal where the amide compound is represented by Formula IV, as follows:

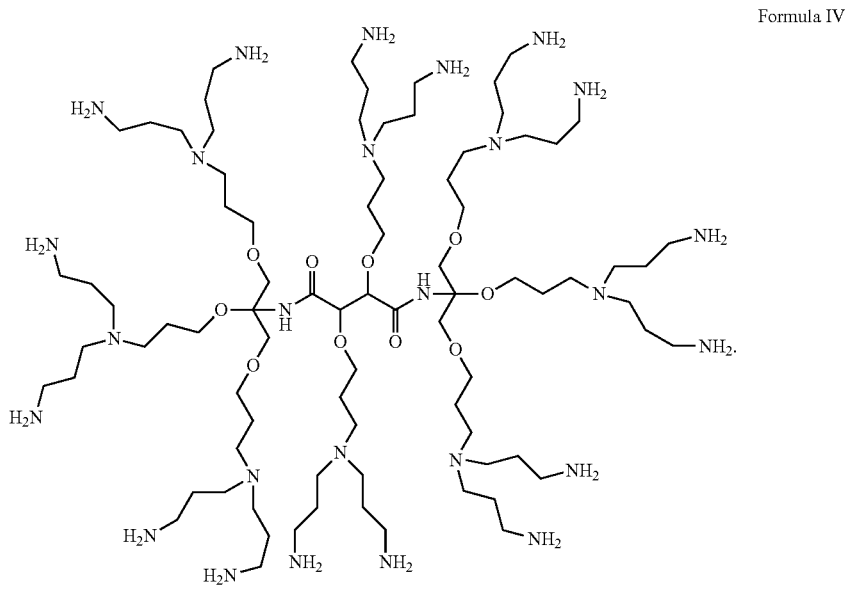 [SMILES: NCCCN(CCCN)CCCOCC(COCCCN(CCCN)CCCN)(NC(=O)C(OCCCN(CCCN)CCCN)C(OCCCN(CCCN)CCCN)C(=O)NC(COCCCN(CCCN)CCCN)(COCCCN(CCCN)CCCN)OCCCN(CCCN)CCCN)OCCCN(CCCN)CCCN]

Formula IV

In some embodiments, the present invention is an amide compound, an amide polymer (comprising or derived from said amide compound or a residue thereof), a pharmaceutical composition (comprising or derived from said amide compound or a residue thereof or comprising or derived from said amide polymer or a residue thereof) or a method of using the same in a therapeutically effective amount to remove a compound or ion, such as a phosphorous-containing compound or a phosphorous-containing ion (e.g. phosphate), from the gastrointestinal tract of an animal where the amide compound is represented by Formula V, as follows:

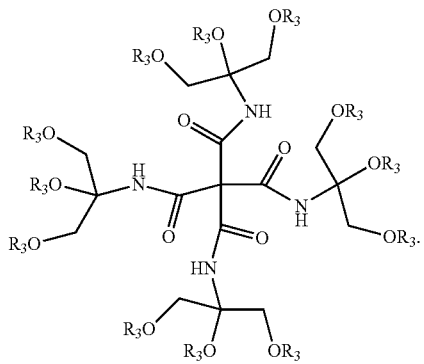

Formula V wherein $R_3$ independently represents a group represented by Formula II, Formula IIa, or Formula IIb as defined above.

In some embodiments, the present invention is an amide compound, an amide polymer (comprising or derived from said amide compound or a residue thereof), a pharmaceutical composition (comprising or derived from said amide compound or a residue thereof or comprising or derived from said amide polymer or a residue thereof) or a method of using the same in a therapeutically effective amount to remove a compound or ion, such as a phosphorous-containing compound or a phosphorous-containing ion (e.g. phosphate), from the gastrointestinal tract of an animal where the amide compound is represented by Formula VI, as follows:

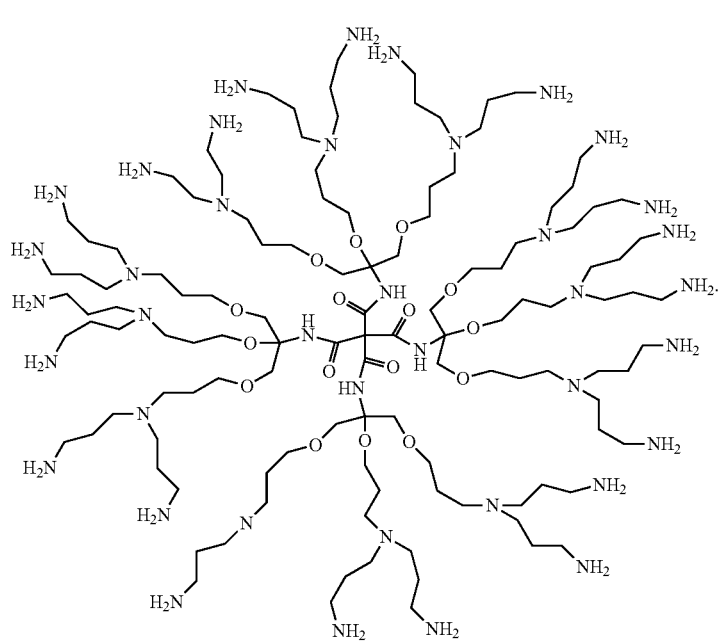

Formula VI

In some embodiments, the present invention is an amide compound, an amide polymer (comprising or derived from said amide compound or a residue thereof), a pharmaceutical composition (comprising or derived from said amide compound or a residue thereof or comprising or derived from said amide polymer or a residue thereof) or a method of using the same in a therapeutically effective amount to remove a compound or ion, such as a phosphorous-containing compound or a phosphorous-containing ion (e.g. phosphate), from the gastrointestinal tract of an animal where the amide polymer comprises at least one amide compound or residue thereof, where the amide compound comprises a substituted amide polyol or residue thereof. The amide polyol may comprise a residue of a substituted or unsubstituted organic polyacid or ester thereof and a residue of a substituted or unsubstituted amine polyol. The amide polyol may be substituted with one or more groups represented by Formula II, Formula IIa, or Formula IIb as defined above.

In some embodiments, the present invention is an amide compound, an amide polymer (comprising or derived from said amide compound or a residue thereof), a pharmaceutical composition (comprising or derived from said amide compound or a residue thereof or comprising or derived from said amide polymer or a residue thereof) or a method of using the same in a therapeutically effective amount to remove a compound or ion, such as a phosphorous-containing compound or a phosphorous-containing ion (e.g. phosphate), from the gastrointestinal tract of an animal where the amide polymer comprises at least one amide compound or residue thereof, where the amide compound comprises an amide dendrimer or residue thereof, the amide dendrimer comprising a substituted amide polyol or residue thereof and a residue or one or more substituted or unsubstituted α, β unsaturated nitriles or residues thereof. In some embodiments, the amide polyol may comprise a residue of a substituted or unsubstituted organic polyacid or ester thereof and a residue of a substituted or unsubstituted amine polyol.

In some embodiments, the present invention is an amide compound, an amide polymer (comprising or derived from said amide compound or a residue thereof), a pharmaceutical composition (comprising or derived from said amide compound or a residue thereof or comprising or derived from said amide polymer or a residue thereof) or a method of using the same in a therapeutically effective amount to remove a compound or ion, such as a phosphorous-containing compound or a phosphorous-containing ion (e.g. phosphate), from the gastrointestinal tract of an animal where the amide compound comprises a substituted amide polyol having one or more units, for example 2-40 units, such as 3-30, 4-25, 5-20, 6-15 or 8-12 units or 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39 units represented by the group comprising the following Formula VII:

Formula VII

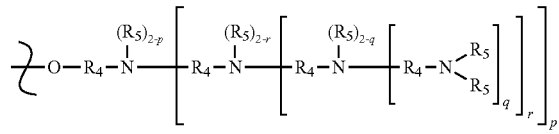

wherein p, q and r independently represent an integer from 0-2, for example, 0, 1 or 2; $R_4$ independently represents

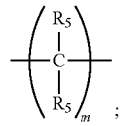

wherein m independently represents an integer from 1-20, for example, 1-15, 1-2, 3-6, 7-10, 11-15, such as 1, 2, 3, 4, 5, 6, 7, 8, 9, 10, 11, 12, 13, 14, 15, 16, 17, 18, 19 or 20; $R_5$ independently represents a hydrogen radical; a substituted or un-substituted alkyl radical; a substituted or un-substituted aryl radical; or $R_5$ and a neighboring $R_5$ together represent a link or links comprising a residue of a crosslinking agent, for example epichlorohydrin or other crosslinking agents, a substituted or un-substituted alicyclic radical, a substituted or un-substituted aromatic radical, or a substituted or un-substituted heterocyclic radical; or $R_5$ represents a link with another compound or a residue thereof.

In some embodiments, the present invention is an amide compound, an amide polymer (comprising or derived from said amide compound or a residue thereof), a pharmaceutical composition (comprising or derived from said amide compound or a residue thereof or comprising or derived from said amide polymer or a residue thereof) or a method of using the same in a therapeutically effective amount to remove a compound or ion, such as a phosphorous-containing compound or a phosphorous-containing ion (e.g. phosphate), from the gastrointestinal tract of an animal where the amide polymer comprises an amide dendrimer or residue thereof, the dendrimer comprising a core that is a residue of one or more substituted or un-substituted organic polyacids or esters thereof and a residue of one or more amine polyols and the dendrimer further comprising a residue of one or more substituted or un-substituted α, β unsaturated nitriles.

In some embodiments, dendrimers of the present invention may be formed from any suitable reaction scheme. Dendrimers are macromolecular compounds that comprise a core that includes functional groups and dendritic branches that may be formed through a series of iterative reaction sequences starting with the functional groups on the core to form a branched macromolecule. In some embodiments the reactive functional groups comprise hydroxyl groups and/or amine groups. The functional groups will have functionalities that are dependent on the type of group. For example, hydroxyl groups have a functionality of one, while primary amines generally have a functionality of 2, though they may be quaternized. In some embodiments, an amide polymer comprises a dendrimer or residue thereof. In some embodiments, the dendrimer may comprise an amide polyol core that is a residue of one or more organic polyacids or esters thereof and a residue of one or more amine polyols, with the dendrimer further comprising a residue of one or more substituted or un-substituted α, β unsaturated nitriles. The amide polymer may further comprise a crosslinking or other linking agent or residue thereof. Some examples of substituted or un-substituted α, β unsaturated nitriles include methacrylonitrile and acrylonitrile.

In some embodiments, amide dendrimers of the present invention are prepared by reaction of an amide polyol core that is reacted with substituted or un-substituted α, β unsaturated nitriles and subsequently reduced, resulting in dendritic branching. An amide polyol core may be formed by reaction of an amine polyol with an organic polyacid or ester thereof to form the amide polyol. An example of an amide polyol formed by this reaction is set forth in Scheme IA, using tartaric acid as the polyacid and 2-aminopropane-1,2,3-triol as the polyol:

Scheme IA

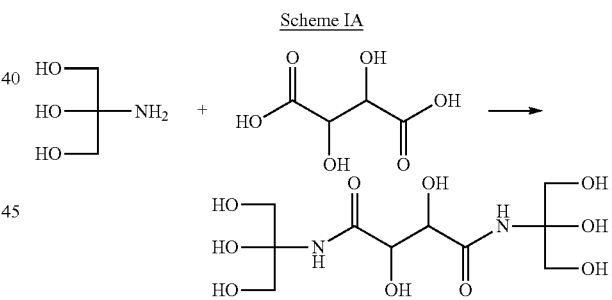

The amide polyol may then be reacted by Michael addition of a substituted or un-substituted α, β unsaturated nitrile to one or more of the hydroxyl groups on the amide polyol core to replace the hydrogen of one or more hydroxyl groups with one or more alkyl cyanide groups, resulting in an ether linkage to the core via the oxygen atom of the hydroxyl groups. The nitriles of the alkyl cyanide groups of the resulting compound are then chemically reduced, for example via hydrogenation, to form the corresponding primary amines. The Michael addition and subsequent reduction may be performed on the primary amines yielding branched tertiary or secondary amines terminating in primary amines. Subsequent Michael additions and reductions may be repeated one or more times to provide the branched structure characteristic of dendrimers. A schematic of this process is provided below in Scheme IB, using the amide polyol from Scheme IA as the polyol and acrylonitrile as the α, β unsaturated nitrile:

SCHEME IB
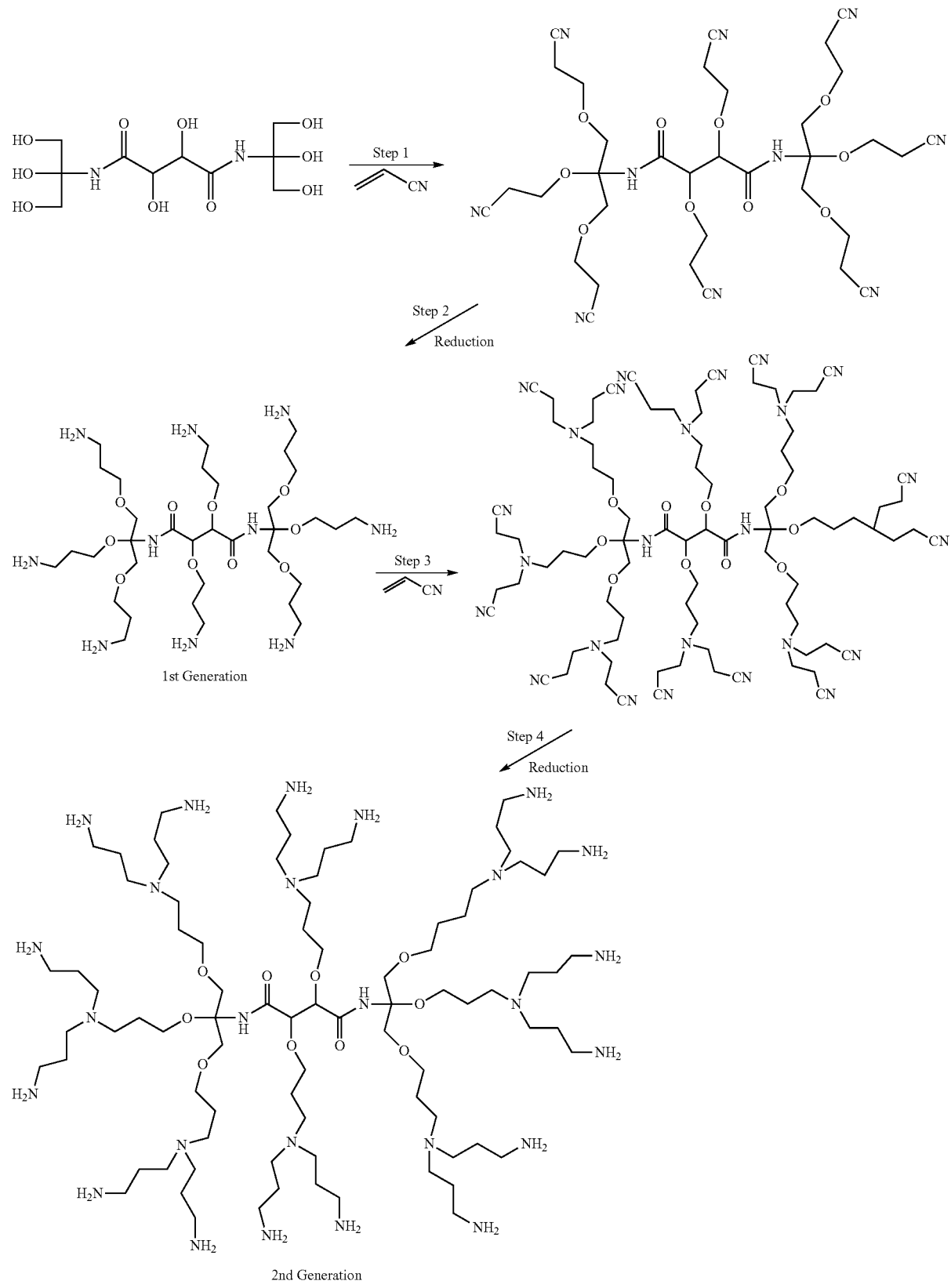
3rd, 4th and subsequent generations may be formed by one or more repetitions of Steps 3 and 4.

In some embodiments, each iteration of Michael addition and subsequent reduction may be considered one generation. Thus, for some embodiments, a compound having one generation of dendritic branching may have undergone one iteration of Michael addition and reduction, compounds having two generations of dendritic branching may have undergone two iterations of Michael addition and reduction, compounds having three generations of dendritic branching may have undergone three iterations of Michael addition and reduction, compounds having four generations of dendritic branching may have undergone four iterations of Michael addition and reduction, etc. Generally dendrimers according to some embodiments of the present invention may have from 1-10, such as 2, 3, 4, 5, 6, 7, 8, or 9 generations of dendritic branching.

In some embodiments, a method of making an amide polymer comprises reacting an organic polyacid or an ester thereof with an amine polyol to form an amide polyol core, reacting the amide polyol core with a substituted or un-substituted α, β unsaturated nitrile using a Michael addition reaction to form a polyether, reducing at least one nitrile group on the polyether to form a primary amine, repeating the Michael addition and reduction on the at least one primary amine one or more times to form an amide dendrimer; and crosslinking the amide dendrimer with a crosslinking agent to form an amide polymer.

In some embodiments, the present invention is a polymer network, a pharmaceutical composition (comprising or derived from polymer network or a residue thereof) or a method of using the same in a therapeutically effective amount to remove a compound or ion, such as a phosphorous-containing compound or a phosphorous-containing ion (e.g. phosphate), from the gastrointestinal tract of an animal where the a polymer network comprises two or more amide polymers or residues thereof. The polymer network may comprise a residue of two or more substituted or un-substituted amide polyols, a residue of one or more substituted or un-substituted α, β unsaturated nitrile groups and a residue of one or more crosslinking or other linking agents. In some embodiments, the polymer network comprises residues of two or more polyethers, where the polyethers comprise a residue of one or more amide polyols and a residue of one or more substituted or un-substituted α, β unsaturated nitrile groups, and where the network also comprises a residue of one or more crosslinking agents. In some embodiments, the polymer network may include one or more amide dendrimers or residues thereof.

In some embodiments, the present invention is an amide compound, an amide polymer (comprising or derived from said amide compound or a residue thereof), a pharmaceutical composition (comprising or derived from said amide compound or a residue thereof or comprising or derived from said amide polymer or a residue thereof) or a method of using the same in a therapeutically effective amount to remove a compound or ion, such as a phosphorous-containing compound or a phosphorous-containing ion (e.g. phosphate), from the gastrointestinal tract of an animal where the amide polymer comprises two or more amide dendrimers or residues thereof represented by Formula V, wherein R₃ independently represents a group represented by Formula II, Formula IIa, or Formula IIb as defined above.

In some embodiments, the present invention is an amide polymer (comprising or derived from an amide compound or a residue thereof), a pharmaceutical composition (comprising or derived from said amide polymer or a residue thereof), a polymer network (comprising or derived from said amide polymer or a residue thereof) or a method of using the same in a therapeutically effective amount to remove a compound or ion, such as a phosphorous-containing compound or a phosphorous-containing ion (e.g. phosphate), from the gastrointestinal tract of an animal, the amide polymer, polymer network or composition having a plurality of units represented by the following Formula VIII:

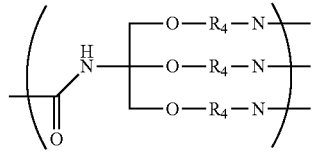

Formula VIII wherein $R_4$ independently represents

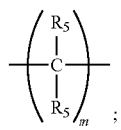

wherein m independently represents an integer from 1-20, for example, 1-15, 1-2, 3-6, 7-10, 11-15, such as 1, 2, 3, 4, 5, 6, 7, 8, 9, 10, 11, 12, 13, 14, 15, 16, 17, 18, 19 or 20; $R_5$ independently represents a hydrogen radical; a substituted or un-substituted alkyl radical; a substituted or un-substituted aryl radical; or $R_5$ and a neighboring $R_5$ together represent a link or links comprising a residue of a crosslinking agent, for example epichlorohydrin or other crosslinking agents, a substituted or un-substituted alicyclic radical, a substituted or un-substituted aromatic radical, or a substituted or un-substituted heterocyclic radical; or $R_5$ represents a link with another compound or a residue thereof;

and a plurality of units represented by the following Formula IX:

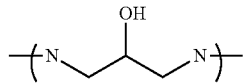

In some embodiments, the invention is a method for reducing blood phosphate levels by 5-100% in a patient in need thereof, the method comprising administering a therapeutically effective amount of an amide polymer, amine polyether polymer or composition to the patient, where the amide polymer or composition comprises an amide compound or residue thereof, the amide compound represented by Formula I. In some embodiments, the invention is a method for reducing urinary phosphorous by 5-100% in a patient in need thereof, the method comprising administering a therapeutically effective amount of an amide polymer, amine polyether polymer or composition to the patient, where the amide polymer or composition comprises an amide compound or residue thereof, the amide compound represented by Formula I or a residue thereof.

In some embodiments, the present invention is an amine polyether compound, an amine polyether polymer (comprising or derived from said amine polyether compound or a residue thereof), a pharmaceutical composition (comprising or derived from said amine polyether compound or a residue thereof or comprising or derived from said amine polyether polymer or a residue thereof) or a method of using the same in a therapeutically effective amount to remove a compound or ion, such as a phosphorous-containing compound or a phosphorous-containing ion (e.g. phosphate), from the gastrointestinal tract of an animal where the amine polyether compound is represented by Formula X, as follows:

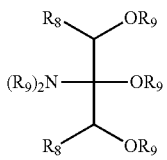

Formula X wherein $R_8$ independently represents a hydrogen radical or $-OR_9$ and $R_9$ independently represents a hydrogen radical or a group represented by Formula II, Formula IIa or Formula IIb as defined above.

In some embodiments, amine polyol compounds that may be used to form the amide polyol cores for, or in the preparation of amide compounds, amide polymers, polymer networks and compositions according to some embodiments of the invention include any amine polyols and in some embodiments may be represented by the following general molecular formula:

$$N_a R_6 (OH)_c$$

where a independently represents an integer from 1 to 6, for example 1, 2, 3, 4, 5 or 6; c independently represents an integer from 1-10, for example 1, 2, 3, 4, 5, 6, 7, 8, 9, 10 and $R_6$ independently represents a branched or unbranched, substituted or unsubstituted $C_1$ to $C_{10}$ alkyl group.

In some embodiments, examples of some suitable amine polyols include amine-substituted polyhydric alcohols. Examples of some polyhydric alcohols that may be amine substituted to form suitable amine polyols include 1,4-butanediol, 1,5-pentanediol, 1,6-hexanediol, 1,6-cyclohexanedimethanol, 2-methyl-1,3-propanediol, 2-methyl-2-ethyl-1,3-propanediol, 2-ethyl-2-butyl-1,3-propanediol, neopentyl glycol, dimethylolpropane, 1,1-dimethylolcyclohexane, glycerol, trimethylolethane, trimethylolpropane, diglycerol, ditrimethylolethane, ditrimethylolpropane, pentaerythritol, dipentaerythritol and sugar alcohols.

Sugar alcohols that may be amine substituted to form suitable amine polyols include sugar alcohols derived from aldoses and ketoses including those derived from monoses, dioses, trioses, tetroses, pentoses, hexoses, heptoses, octoses and nonoses. The aldoses and ketoses from which the sugar alcohols are derived may be fully or partially hydrogenated, and may be substituted, including replacement of one or more hydroxyl groups on the aldose or ketose with one or more hydrogen groups to form the corresponding deoxyaldose or deoxyketose, provided that at least two alcohol groups remain. Specific examples of aldoses and ketoses from which suitable sugar alcohols may be derived include: erythrose, threose, ribose, deoxyribose, arabinose, xylose, lyxose, allose, altrose, glucose, mannose, gulose, idose, galactose, talose, ribulose, xylulose, fructose, psicose, tagatose, mannoheptulose, sedoheptulose, sorbose, pentaerythrose, octolose, sialose or a partially or fully hydrogenated derivatives thereof, or a combinations thereof. Non-limiting examples of some suitable sugar alcohols that may be amine substituted include sorbitol, mannitol, xylitol, erythritol, galactitol, dulcitol, arabitol, threitol, arabinitol, ribitol, and rhamnitol.

In some embodiments, suitable amine polyol compounds that may be used to form the cores for, or in the preparation of amide compounds, amide polymers, polymer networks and compositions according to some embodiments of the invention include:

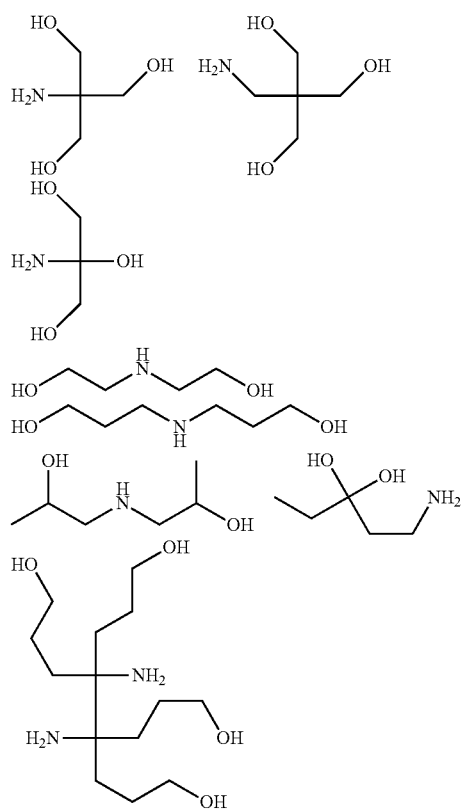

In some embodiments, the invention includes amine polyether compounds that may be formed from any of the amine polyols described herein. In some embodiments, the amine polyether compounds are formed via Michael addition and reduction on the hydroxyl groups and/or amine groups of the amine polyols similar to the reaction described above with respect to the amide polyols. The resulting amine polyether compounds may be crosslinked to form amine polyether polymers. The amine polyether compounds and amine polyether polymers may be used in pharmaceutical compositions, polymer networks and methods of treatment as described herein with respect to the amide polymers and compositions.

In some embodiments, organic polyacids and/or esters thereof may be used to form the cores for, or in the preparation of, amide compounds, amide polymers, polymer networks and compositions according to some embodiments of the invention. Esters of all of the organic polyacids may be used instead of, or in conjunction with, the organic polyacids, including polyacids that are partially and fully esterified. Examples of the polyacids include any organic polyacids, including diacids, triacids, tetracids, pentacids and hexacids. Examples of some polyacids that may be used include substituted or un-substituted methanetetracarboxylic acid, ethane-1,1,2,2-tetracarboxylic acid, oxalic acid, malonic acid, succinic acid, fumaric acid, maleic acid, glutaric acid, adipic acid, pimelic acid, suberic acid, azelaic acid, sebacic acid, tartaric acid, tartronic, 3-hydroxypentanedioc acid, 3,4-hydroxyhexanedioc acid, glucaric acid, mucic acid, galactaric acid, xylaric acid, aspartic acid, 2-amino malonic acid, citric acid, ethylenediaminetetraacetic acid. In some embodiments, the organic polyacids include one or more substitutions, where the substitutions comprise hydroxyl and/or amine groups.

In some embodiments, suitable organic polyacids that may be used to form the cores for, or in the preparation of, amide compounds, amide polymers, polymer networks and compositions according to some embodiments of the invention include aldaric acids having the following general formula:

HOOC—(CHOH)$_w$—COOH wherein w represents an integer from 1 to 20, for example, 1-15, 1-2, 3-6, 7-10, 11-15, such as 1, 2, 3, 4, 5, 6, 7, 8, 9, 10, 11, 12, 13, 14, 15, 16, 17, 18, 19 or 20. Additional examples of suitable aldaric acids include diacids formed from any of the sugar alcohols as mentioned above. In some embodiments, one or more of the non-acid hydroxyl groups of the aldaric acids may be replaced with an amine group.

In some embodiments, suitable organic polyacids may be cyclic polyacids such as aromatic, alicyclic or heterocyclic polyacids having a 3, 4, 5 or 6 membered ring or rings that are partially or fully substituted with carboxylic acid groups. For example, a 3-membered polyacid ring may have 2, or 3 carboxylic acid groups, a 6-membered polyacid ring may have 2, 3, 4, 5, or 6 carboxylic acid groups and a naphthalene group may have 2, 3, 4, 5, 6, 7 or 8 carboxylic acid groups. The heterocyclic organic polyacids may be aromatic or non-aromatic and may have up to four heteroatoms selected from N, O and S and combinations thereof. The cyclic polyacids may additionally have non-acid substitutions on the rings including, for example, —OH groups.

Examples of some aromatic, alicyclic and heterocyclic groups that may be substituted with at least 2 carboxylic acids to form suitable organic polyacids include cyclopropyl, cyclobutyl, cyclopentyl, cyclohexyl, piperidinyl, piperizinyl, thiazolidinyl, imidazolidinyl, pyranyl, tetrahydrofuranyl, oxanyl, benzyl, pyridinyl, imidazolyl, pyrazolyl, thiazolyl, oxazolyl, pyrimidinyl, dioxanyl, quinizolinyl, indolinyl, benzothiazolyl, benzooxazolyl, pyrazinyl, furanyl, thenyl, naphthalenyl and the like.

Non-limiting examples of some suitable cyclic polyacids include: cyclohexane-1,2-dicarboxylic acid, cyclohexane-1,3-dicarboxylic acid, cyclohexane-1,4-dicarboxylic acid, cyclohexane-1,2,3-tricarboxylic acid, cyclohexane-1,2,4-tricarboxylic acid, cyclohexane-1,3,4-tricarboxylic acid, cyclohexane-1,3,5-tricarboxylic acid, cyclohexane-1,2,3,4-tetracarboxylic acid, cyclohexane-1,3,4,5-tetracarboxylic acid, cyclohexane-1,2,3,4,5-pentacarboxylic acid, cyclohexane-1,2,3,4,5,6-hexacarboxylic acid, cyclopentane-1,2-dicarboxylic acid, cyclopentane-1,3-dicarboxylic acid, cyclopentane-1,2-dicarboxylic acid, cyclopentane-1,2,3-tricarboxylic acid, cyclopentane-1,2,4-tricarboxylic acid, cyclopentane-1,2,3,4-tetracarboxylic acid, cyclopentane-1,2,3,4,5-pentacarboxylic acid, phthahlic acid, isophthalic acid, terephthalic acid, hemimellitic acid, trimellitic acid, trimesic acid, benzene-1,2,3,4-tetracarboxylic acid, benzene-1,2,3,5-tetracarboxylic acid, pyromellitic acid, benzene-1,2,3,4,5-pentacarboxylic acid, mellitic acid, quinolinic acid, 1H-pyrazole-3,4-dicarboxylic acid, 1H-pyrazole-1,3,4-tricarboxylic acid, pyridine-2,4,5-tricarboxylic acid.

Examples of some suitable organic polyacids include:

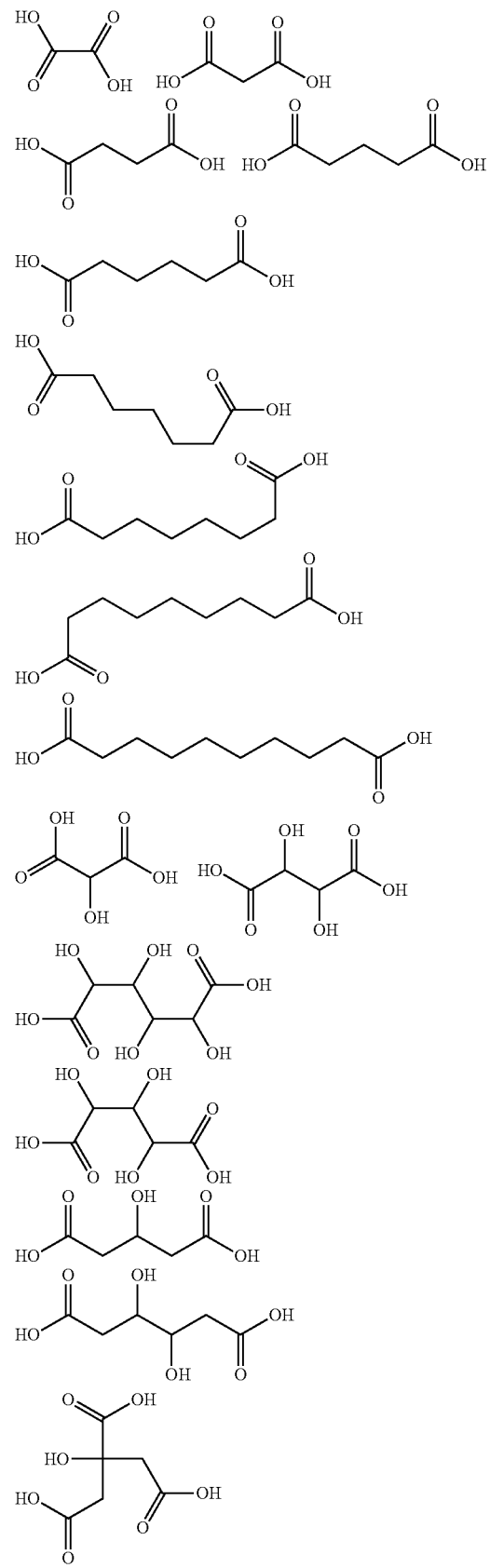

-continued

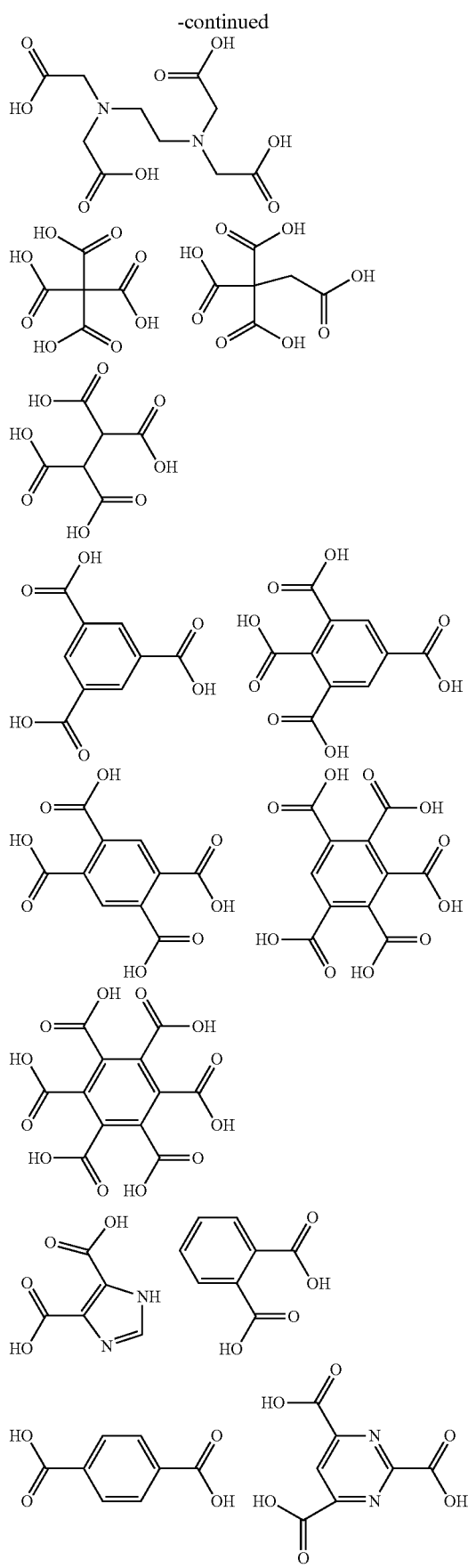
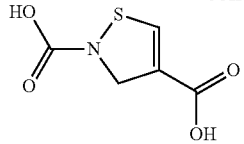
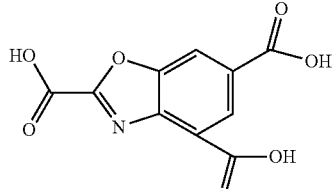
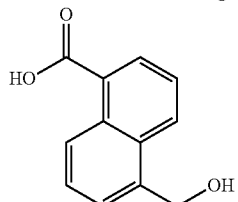
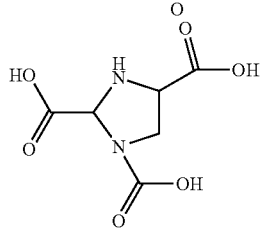

In some embodiments, the present invention is an amide compound, an amide polymer (comprising or derived from said amide compound or a residue thereof), a pharmaceutical composition (comprising or derived from said amide compound or a residue thereof or comprising or derived from said amide polymer or a residue thereof) or a method of using the same in a therapeutically effective amount to remove a compound or ion, such as a phosphorous-containing compound or a phosphorous-containing ion (e.g. phosphate), from the gastrointestinal tract of an animal where the amide compound is represented by Formula XI, as follows:

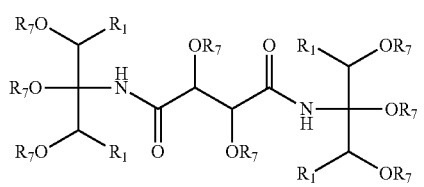

Formula XI wherein $R_1$ is as defined above for Formula I, and $R_7$ independently represents H or a group represented by Formula II, Formula IIa, or Formula IIb as defined above.

In some embodiments, the present invention is an amide compound, an amide polymer (comprising or derived from said amide compound or a residue thereof), a pharmaceutical composition (comprising or derived from said amide compound or a residue thereof or comprising or derived from said amide polymer or a residue thereof) or a method of using the same in a therapeutically effective amount to remove a compound or ion, such as a phosphorous-containing compound or a phosphorous-containing ion (e.g. phosphate), from the gastrointestinal tract of an animal where the amide compound is represented by Formula XII, as follows:

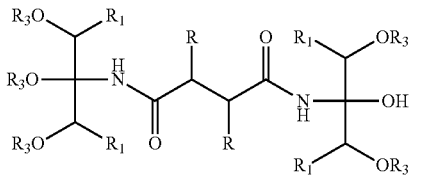

Formula XII wherein R and $R_1$ are as defined above for Formula I, and $R_3$ independently represents a group represented by Formula II, Formula IIa, or Formula IIb as defined above.

In some embodiments, the present invention is an amide compound, an amide polymer (comprising or derived from said amide compound or a residue thereof), a pharmaceutical composition (comprising or derived from said amide compound or a residue thereof or comprising or derived from said amide polymer or a residue thereof) or a method of using the same in a therapeutically effective amount to remove a compound or ion, such as a phosphorous-containing compound or a phosphorous-containing ion (e.g. phosphate), from the gastrointestinal tract of an animal where the amide compound is represented by Formula XIII, as follows:

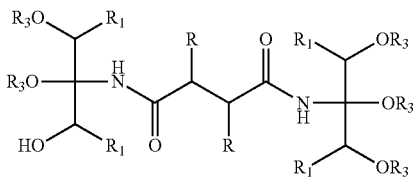

Formula XIII wherein R and $R_1$ are as defined above for Formula I, and $R_3$ independently represents a group represented by Formula II, Formula IIa, or Formula IIb as defined above.

In some embodiments, the present invention is an amide compound, an amide polymer (comprising or derived from said amide compound or a residue thereof), a pharmaceutical composition (comprising or derived from said amide compound or a residue thereof or comprising or derived from said amide polymer or a residue thereof) or a method of using the same in a therapeutically effective amount to remove a compound or ion, such as a phosphorous-containing compound or a phosphorous-containing ion (e.g. phosphate), from the gastrointestinal tract of an animal where the amide compound is represented by Formula XIV, as follows:

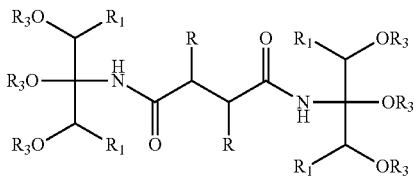

Formula XIV wherein R and $R_1$ are as defined above for Formula I, and $R_3$ independently represents a group represented by Formula II, Formula IIa, or Formula IIb as defined above.

In some embodiments, the present invention is an amide compound, an amide polymer (comprising or derived from said amide compound or a residue thereof), a pharmaceutical composition (comprising or derived from said amide compound or a residue thereof or comprising or derived from said amide polymer or a residue thereof) or a method of using the same in a therapeutically effective amount to remove a compound or ion, such as a phosphorous-containing compound or a phosphorous-containing ion (e.g. phosphate), from the gastrointestinal tract of an animal where the amide compound is represented by Formula XV, as follows:

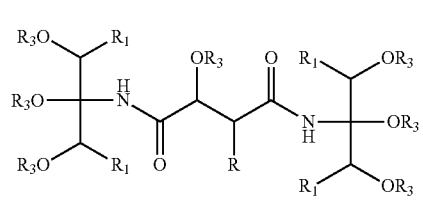

Formula XV wherein R and $R_1$ are as defined above for Formula I, and $R_3$ independently represents a group represented by Formula II, Formula IIa, or Formula IIb as defined above.

In some embodiments, the present invention is an amide compound, an amide polymer (comprising or derived from said amide compound or a residue thereof), a pharmaceutical composition (comprising or derived from said amide compound or a residue thereof or comprising or derived from said amide polymer or a residue thereof) or a method of using the same in a therapeutically effective amount to remove a compound or ion, such as a phosphorous-containing compound or a phosphorous-containing ion (e.g. phosphate), from the gastrointestinal tract of an animal where the amide compound is represented by Formula XVI, as follows:

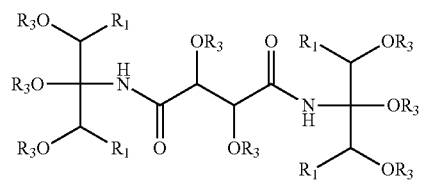

Formula XVI wherein $R_1$ is as defined above for Formula I, and $R_3$ independently represents a group represented by Formula II, Formula IIa, or Formula IIb as defined above.

In some embodiments, the present invention is an amide compound, an amide polymer (comprising or derived from said amide compound or a residue thereof), a pharmaceutical composition (comprising or derived from said amide compound or a residue thereof or comprising or derived from said amide polymer or a residue thereof) or a method of using the same in a therapeutically effective amount to remove a compound or ion, such as a phosphorous-containing compound or a phosphorous-containing ion (e.g. phosphate), from the gastrointestinal tract of an animal where the amide compound is represented by Formula XVII, as follows:

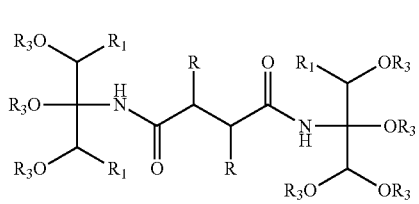

Formula XVII wherein R and $R_1$ are as defined above for Formula I, and $R_3$ independently represents a group represented by Formula II, Formula IIa, or Formula IIb as defined above.

In some embodiments, the present invention is an amide compound, an amide polymer (comprising or derived from said amide compound or a residue thereof), a pharmaceutical composition (comprising or derived from said amide compound or a residue thereof or comprising or derived from said amide polymer or a residue thereof) or a method of using the same in a therapeutically effective amount to remove a compound or ion, such as a phosphorous-containing compound or a phosphorous-containing ion (e.g. phosphate), from the gastrointestinal tract of an animal where the amide compound is represented by Formula XVIII, as follows:

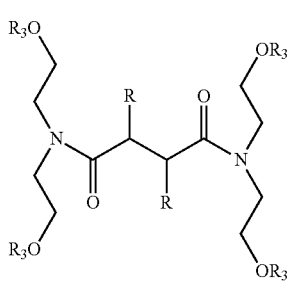

Formula XVIII wherein R is as defined above for Formula I and $R_3$ independently represents a group represented by Formula II, Formula IIa, or Formula IIb as defined above.

In some embodiments, the present invention is an amide compound, an amide polymer (comprising or derived from said amide compound or a residue thereof), a pharmaceutical composition (comprising or derived from said amide compound or a residue thereof or comprising or derived from said amide polymer or a residue thereof) or a method of using the same in a therapeutically effective amount to remove a compound or ion, such as a phosphorous-containing compound or a phosphorous-containing ion (e.g. phosphate), from the gastrointestinal tract of an animal where the amide compound is represented by Formula XIX, as follows:

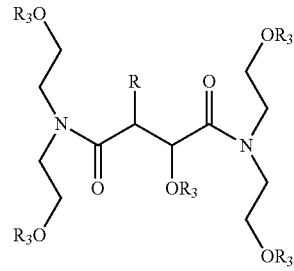

Formula XIX wherein $R_1$ is as defined above for Formula I and $R_3$ independently represents a group represented by Formula II, Formula IIa, or Formula IIb as defined above.

In some embodiments, the present invention is an amide compound, an amide polymer (comprising or derived from said amide compound or a residue thereof), a pharmaceutical composition (comprising or derived from said amide compound or a residue thereof or comprising or derived from said amide polymer or a residue thereof) or a method of using the same in a therapeutically effective amount to remove a compound or ion, such as a phosphorous-containing compound or a phosphorous-containing ion (e.g. phosphate), from the gastrointestinal tract of an animal where the amide compound is represented by Formula XX, as follows:

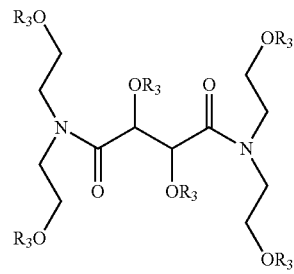

Formula XX wherein $R_3$ independently represents a group represented by Formula II, Formula IIa, or Formula IIb as defined above.

In some embodiments, the present invention is an amide compound, an amide polymer (comprising or derived from said amide compound or a residue thereof), a pharmaceutical composition (comprising or derived from said amide compound or a residue thereof or comprising or derived from said amide polymer or a residue thereof) or a method of using the same in a therapeutically effective amount to remove a compound or ion, such as a phosphorous-containing compound or a phosphorous-containing ion (e.g. phosphate), from the gastrointestinal tract of an animal where the amide compound is represented by Formula XXI, as follows:

Formula XXI

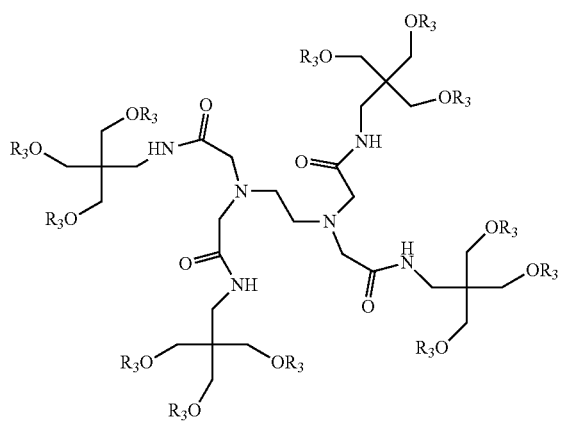

wherein $R_3$ independently represents a group represented by Formula II, Formula IIa, or Formula IIb as defined above.

In some embodiments, the invention is a method of treating a phosphate imbalance disorder such as hyperphosphatemia comprising administering a therapeutically effective amount of an amide polymer or composition to a patient in need thereof. In some embodiments, the amide polymer or composition comprises an amide compound or residue thereof according to Formula I.

In some embodiments, a method of treating a phosphate imbalance disorder such as hyperphosphatemia comprises administering a therapeutically effective amount of an amine polyether polymer, an amide polymer or composition to a patient in need thereof, where the amine polyether polymer or the amide polymer or composition comprises an amine polyether compound or residue thereof or an amide compound or residue thereof represented by at least one of Formulas III-VI, X-XXI or where the amide polymer or composition comprises a plurality of units according to Formula VII, or a plurality of units according to Formulas VIII and IX.

In some embodiments, the amide compound is a mixture of more than one amine polyether compound or amide compound, for example 2-20 such as 2, 3, 4, 5, 6, 7, 8, 9 or 10 amine polyether compounds or amide compounds represented by Formulas I, III-VI or X-XXI. In some embodiments, the mixture predominantly comprises an amine polyether compound or an amide compound represented by one of Formulas I, III, V or X-XXI where q, r and p are independently 0 or 2. For example, in some embodiments a plurality of the mixture, such as greater than 30 wt. %, greater than 40 wt. %, greater than 50 wt. %, greater than 60 wt. % or greater than 70 wt. % based on the total weight of the mixture, comprises an amine polyether compound or residue thereof or an amide compound or residue thereof represented by one of Formulas I, III, V or X-XXI where q, r and p are independently 0 or 2. For example, in some embodiments, the mixture comprises greater than 30 wt %, greater than 40 wt. %, greater than 50 wt. %, greater than 60 wt. % or greater than 70 wt. % of an amide compound or residue thereof represented by Formula IV or Formula VI.

In some embodiments, the invention comprises an amine polyether polymer or an amide polymer, the polymer derived from an amine polyether compound or an amide compound that is a mixture of amine polyether compounds or amide compounds, a pharmaceutical composition comprising such an amine polyether polymer or amide polymer, or a method of using the same in a therapeutically effective amount to remove a compound or ion, such as a phosphorous-containing compound or a phosphorous-containing ion (e.g. phosphate), from the gastrointestinal tract of an animal.

Other embodiments of the invention include pendant amide polymers or pendant amine polyether polymers formed with amide compounds or residues thereof or amine polyether compounds or residues thereof as pendant groups on a polymer or polymerized backbone of a polymer. Such pendant amide polymers and pendant amine polyether polymers may be formed by adding one or more polymerizable groups to one or more amide groups on an amide compound to form an amide monomer or to one or more amine groups on an amine polyether compound to form an amine polyether monomer and then subsequently polymerizing the polymerizable group to form a pendant amide polymer comprising an amide compound or residue thereof or a pendant amine polyether polymer comprising an amine polyether compound or residue thereof. A schematic example of such an addition follows [it should be noted in the following that an amide compound or amine polyether compound designated as "AC" is intended to represent an amide compound or residue thereof or an amine polyether compound or residue thereof, of the invention, with one of its amine groups depicted for purposes of illustrating how a polymerizable group may be added to an amide compound or an amine polyether compound]:

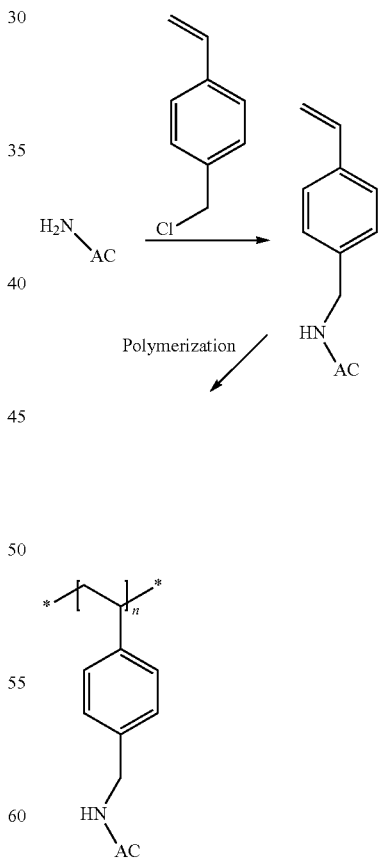

Non-limiting examples of other polymerizable groups that may be used with amide compounds or residues thereof and with amine polyether compounds or residues thereof according to embodiments of the invention include:

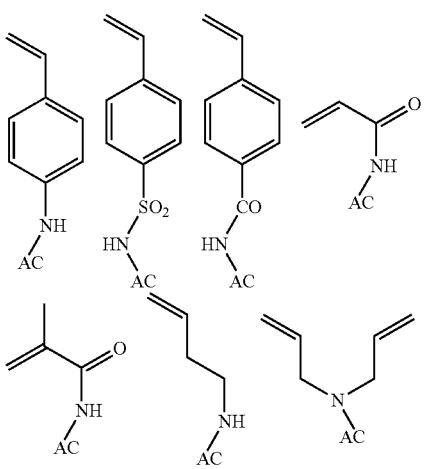

One or more polymerizable groups may be added to each amide compound or amine polyether compound and thus it is possible to have mixtures of amide monomers or amine polyether monomers having various pendant ACs having differing numbers of polymerizable groups. In addition, the pendant amide polymers and pendant amine polyether polymers made in this fashion may be modified, crosslinked, formed into a network or substituted post polymerization. Such modification may be performed for any number of reasons, including to improve efficacy, tolerability or reduce side effects.

Amide monomers may also be formed by addition of amide compounds to amine-reactive polymers by reacting one or more amine groups of the amide monomers with one or more amine-reactive groups on the amine-reactive polymers. Amine polyether monomers may also be formed by addition of amine polyether compounds to amine-reactive polymers by reacting one or more amine groups of the amine polyether monomers with one or more amine-reactive groups on the amine-reactive polymers. Examples of some amine reactive polymers include:

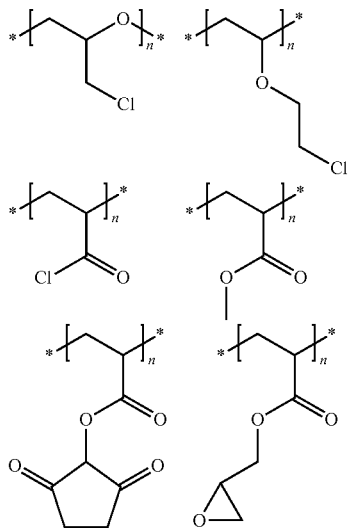

The amide compounds, amide monomers, amine polyether compounds or amine polyether monomers may also serve as multifunctional monomers to form polymers. For example, when the amide compounds or the polymers formed from the amide monomers or the amine polyether compounds or the polymers formed from the amine polyether monomers are crosslinked, the crosslinking reaction may be carried out either in solution of bulk (i.e. using the neat amide and neat crosslinking agents) or in dispersed media. When a bulk process is used, solvents are selected so that they co-dissolve the reactants and do not interfere with the crosslinking reaction. Suitable solvents include water, low boiling alcohols (methanol, ethanol, butanol), dimethylformamide, dimethylsulfoxide, acetone, methylethylketone, and the like.

Other polymerization methods may include a single polymerization reaction, stepwise addition of individual monomers via a series of reactions, the stepwise addition of blocks of monomers, combinations of the foregoing, or any other method of polymerization, such as, for example, direct or inverse suspension, condensation, emulsion, precipitation techniques, polymerization in aerosol or using bulk polymerization/crosslinking methods and size reduction processes such as extrusion and grinding. Processes can be carried out as batch, semi-continuous and continuous processes. For processes in dispersed media, the continuous phase can be selected from apolar solvents such as toluene, benzene, hydrocarbon, halogenated solvents, supercritical carbon dioxide, and the like. With a direct suspension process, water can be used, although salt brines are also useful to "salt out" the amide and crosslinking agents in a droplet separate phase.

Amide compounds, amide monomers, amine polyether compounds and amine polyether monomers of the invention may be copolymerized with one or more other monomers or oligomers or other polymerizable groups, may be crosslinked, may have crosslinking or other linking agents or monomers within the polymer backbone or as pendant groups or may be formed or polymerized to form a polymer network or mixed polymer network comprising: amide compounds or residues thereof, amide monomers or residues thereof, amine polyether compounds or residues thereof, amine polyether monomers or residues thereof, crosslinking agents or residues thereof, or other linking agents or residues thereof. The network may include multiple connections between the same or different molecules that may be direct or may include one or more linking groups such as crosslinking agents or other linking agents such as monomers or oligomers or residues thereof.

Non-limiting examples of comonomers which may be used alone or in combination include: styrene, substituted styrene, alkyl acrylate, substituted alkyl acrylate, alkyl methacrylate, substituted alkyl methacrylate, acrylonitrile, methacrylonitrile, acrylamide, methacrylamide, N-alkylacrylamide, N-alkylmethacrylamide, N,N-dialkylacrylamide, N,N-dialkylmethacrylamide, isoprene, butadiene, ethylene, vinyl acetate, N-vinyl amide, maleic acid derivatives, vinyl ether, allyle, methallyl monomers and combinations thereof. Functionalized versions of these monomers may also be used. Additional specific monomers or comonomers that may be used in this invention include, but are not limited to, methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, α-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, glycidyl methacrylate, 2-hydroxyethyl methacrylate, hydroxypropyl methacrylate (all isomers), hydroxybutyl methacrylate (all isomers), N,N-dimethylamino ethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethacrylamide, N—N-butylmethacrylamide, N-methylolmethacrylamide, N-ethylolmethacrylamide, N-tert-butylacrylamide, N—N-butylacrylamide, N-methylolacrylamide, N-ethylolacrylamide, 4-acryloylmorpholine, vinyl benzoic acid (all isomers), diethylaminostyrene (all isomers), α-methylvinyl benzoic acid (all isomers), diethylamino α-methylstyrene (all isomers), p-vinylbenzene sulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropyl methacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysilylpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, maleic anhydride, N-phenylmaleimide, N-butylmaleimide, N-vinylformamide, N-vinyl acetamide, allylamide, methallylamide, allylalcohol, methyl-vinylether, ethylvinylether, butylvinyltether, butadiene, isoprene, chloroprene, ethylene, vinyl acetate and combinations thereof.

In some embodiments, amide polymers or amine polyether polymers of the invention are crosslinked using crosslinking agents, and may not dissolve in solvents, and, at most, swell in solvents. The swelling ratio may be measured according to the procedure in the Test Methods section below and is typically in the range of about 1 to about 20; for example 2 to 10, 2.5 to 8, 3 to 6 such as less than 5, less than 6, or less than 7. In some embodiments, the amide polymers or amine polyether polymers may include crosslinking or other linking agents that may result in amide polymers or amine polyether polymers that do not form gels in solvents and may be soluble or partially soluble in some solvents.

Crosslinking agents are typically compounds having at least two functional groups that are selected from a halogen group, carbonyl group, epoxy group, ester group, acid anhydride group, acid halide group, isocyanate group, vinyl group, and chloroformate group. The crosslinking agent may be attached to the carbon backbone or to a nitrogen of an amide compound or residue thereof, an amide monomer or residue thereof, an amine polyether compound or residue thereof and/or an amine polyether monomer or residue thereof.

Examples of crosslinking agents that are suitable for synthesis of the polymers or dendrimers of the present invention include, but are not limited to, one or more multifunctional crosslinking agents such as: dihaloalkanes, haloalkyloxiranes, alkyloxirane sulfonates, di(haloalkyl)amides, tri(haloalkyl)amides, diepoxides, triepoxides, tetraepoxides, bis(halomethyl) benzenes, tri(halomethyl) benzenes, tetra(halomethyl) benzenes, epihalohydrins such as epichlorohydrin and epibromohydrin poly(epichlorohydrin), (iodomethyl)oxirane, glycidyl tosylate, glycidyl 3-nitrobenzenesulfonate, 4-tosyloxy-1,2-epoxybutane, bromo-1,2-epoxybutane, 1,2-dibromoethane, 1,3-dichloropropane, 1,2-dichloroethane, 1-bromo-2-chloroethane, 1,3-dibromopropane, bis(2-chloroethyl)amide, tris(2-chloroethyl)amide, and bis(2-chloroethyl)methylamide, 1,3-butadiene diepoxide, 1,5-hexadiene diepoxide, diglycidyl ether, 1,2,7,8-diepoxyoctane, 1,2,9,10-diepoxydecane, ethylene glycol diglycidyl ether, propylene glycol diglycidyl ether, 1,4-butanediol diglycidyl ether, 1,2 ethanedioldiglycidyl ether, glycerol diglycidyl ether, 1,3-diglycidyl glyceryl ether, N,N-diglycidylaniline, neopentyl glycol diglycidyl ether, diethylene glycol diglycidyl ether, 1,4-bis(glycidyloxy)benzene, resorcinol digylcidyl ether, 1,6-hexanediol diglycidyl ether, trimethylolpropane diglycidyl ether, 1,4-cyclohexanedimethanol diglycidyl ether, 1,3-bis-(2,3-epoxypropyloxy)-2-(2,3-dihydroxypropyloxy)propane, 1,2-cyclohexanedicarboxylic acid diglycidyl ester, 2,2'-bis(glycidyloxy) diphenylmethane, bisphenol F diglycidyl ether, 1,4-bis(2',3'-epoxypropyl)perfluoro-n-butane, 2,6-di(oxiran-2-ylmethyl)-1,2,3,5,6,7-hexahydropyrrolo[3,4-f]isoindol-1,3,5,7-tetraone, bisphenol A diglycidyl ether, ethyl 5-hydroxy-6,8-di(oxiran-2-ylmethyl)-4-oxo-4h-chromene-2-carboxylate, bis[4-(2,3-epoxy-propylthio)phenyl]-sulfide, 1,3-bis(3-glycidoxypropyl)tetramethyldisiloxane, 9,9-bis[4-(glycidyloxy)phenyl]fluorine, triepoxyisocyanurate, glycerol triglycidyl ether, N,N-diglycidyl-4-glycidyloxyaniline, isocyanuric acid (S,S,S)-triglycidyl ester, isocyanuric acid (R,R,R)-triglycidyl ester, triglycidyl isocyanurate, trimethylolpropane triglycidyl ether, glycerol propoxylate triglycidyl ether, triphenylolmethane triglycidyl ether, 3,7,14-tris[[3-(epoxypropoxy)propyl]dimethylsilyloxy]-1,3,5,7,9,11,14-heptacyclopentyltricyclo[7.3.3.15,11]heptasiloxane, 4,4'-methylenebis(N,N-diglycidylaniline), bis(halomethyl) benzene, bis(halomethyl)biphenyl and bis(halomethyl) naphthalene, toluene diisocyanate, acrylol chloride, methyl acrylate, ethylene bisacrylamide, pyrometallic dianhydride, succinyl dichloride, dimethylsuccinate. When the crosslinking agent is an alkylhalide compound, a base can be used to scavenge the acid formed during the reaction. Inorganic or organic bases are suitable. NaOH is preferred. The base to crosslinking agent ratio is preferably between about 0.5 to about 2.

In some embodiments, the crosslinking agents may be introduced into the polymerization reaction in an amount of from 0.5 to 25 wt. % based on the total weight of the amide polymer or amine polyether polymer, such as from about 2 to about 15 wt. %, from about 2 to about 12 wt. %, from about 3 to about 10 wt. %, or from about 3 to about 6 wt. %, such as 2, 3, 4, 5, 6 wt %. The amount of crosslinking agent necessary may depend on the extent of branching within the amide compound or amine polyether compound.

In some embodiment the molecular weight of the amide polymers or amine polyether polymers, may be typically at least about 1000. For example, the molecular weight may be from about 1000 to about 1,000,000, such as about 1000 to about 750,000, about 1000 to about 500,000, about 1000 to about 250,000, about 1000 to about 100,000 such as less than 750,000, less than 500,000, 250,000 or less than 100,000.

In some embodiments, the pharmaceutical composition of the present invention comprises an amide polymer comprising at least one amide compound or residue thereof, where the amide compound is represented by Formula III where $R_5$ independently represents an H radical or an alkyl radical, q and r are 0 and p is 2, m independently represents an integer from 3-6, such as 3, 4, 5 or 6; and 2-6 wt. % crosslinking agent or residue thereof, such as 2 wt. %, 3 wt. %, 4 wt. %, 5 wt. % or 6 wt. % crosslinking agent, where the crosslinking agent is epichlorohydrin, poly(epichlorohydrin), 1,2-dibromoethane, tris(2-chloroethyl)amide or 1,4-butanediol diglycidyl ether. Another pharmaceutical composition embodiment of the present invention comprises an amide polymer comprising at least one amide compound or residue thereof, where the amide compound is represented by Formula III where $R_5$ independently represents an H radical or an alkyl radical, q is 0 and r and p both are 2, m independently represents an integer from 3-6, such as 3, 4, 5 or 6, where the compound is crosslinked with a crosslinking agent as defined above in this paragraph. A further pharmaceutical composition embodiment of the present invention comprises an amide polymer comprising at least one amide compound or residue thereof, where the amide compound is represented by Formula III where $R_5$ independently represents an H radical or an alkyl radical, q, r and p are each 2, m independently represents an integer from 3-6, such as 3, 4, 5 or 6, where the compound is crosslinked with a crosslinking agent as defined above in this paragraph.

In some embodiments, the pharmaceutical composition of the present invention comprises an amide polymer comprising at least one amide compound or residue thereof, where the amide compound is represented by Formula V where $R_5$ independently represents an H radical or an alkyl radical, q and r are 0 and p is 2, m independently represents an integer from 3-6, such as 3, 4, 5 or 6; and 2-6 wt. % crosslinking agent or residue thereof, such as 2 wt. %, 3 wt. %, 4 wt. %, 5 wt. % or 6 wt. % crosslinking agent, where the crosslinking agent is epichlorohydrin, poly(epichlorohydrin), 1,2-dibromoethane, tris(2-chloroethyl)amide or 1,4-butanediol diglycidyl ether. Another pharmaceutical composition embodiment of the present invention comprises an amide polymer comprising at least one amide compound or residue thereof, where the amide compound is represented by Formula V, where $R_5$ independently represents an H radical or an alkyl radical, q is 0 and r and p both are 2, m independently represents an integer from 3-6, such as 3, 4, 5 or 6, where the compound is crosslinked with a crosslinking agent as defined above in this paragraph. A further pharmaceutical composition embodiment of the present invention comprises an amide polymer comprising at least one amide compound or residue thereof, where the amide compound is represented by Formula V where $R_5$ independently represents an H radical or an alkyl radical, q, r and p are each 2, m independently represents an integer from 3-6, such as 3, 4, 5 or 6, where the compound is crosslinked with a crosslinking agent as defined above in this paragraph.

Another pharmaceutical composition of the present invention comprises an amide polymer comprising an amide compound or residue thereof, the amide compound comprising a substituted amide polyol having one or more units represented by Formula VII where $R_5$ independently represents an H radical or an alkyl radical, q and r are 0 and p is 2, m independently represents an integer from 3-6, such as 3, 4, 5 or 6; and 2-6 wt. % crosslinking agent or residue thereof, such as 2 wt. %, 3 wt. %, 4 wt. %, 5 wt. % or 6 wt. % crosslinking agent, where the crosslinking agent is epichlorohydrin, poly(epichlorohydrin), 1,2-dibromoethane, tris(2-chloroethyl)amide or 1,4-butanediol diglycidyl ether. Another pharmaceutical composition embodiment of the present invention comprises an amide polymer comprising an amide compound or residue thereof, the amide compound comprising a substituted amide polyol having one or more units represented by Formula VII where $R_5$ independently represents an H radical or an alkyl radical, q is 0 and r and p both are 2, m independently represents an integer from 3-6, such as 3, 4, 5 or 6, and crosslinked with a crosslinking agent as defined above in this paragraph. A further pharmaceutical composition embodiment of the present invention comprises an amide polymer comprising an amide compound or residue thereof, the amide compound comprising a substituted amide polyol having one or more units represented by Formula VII where $R_5$ independently represents an H radical or an alkyl radical, q, r and p are each 2, m independently represents an integer from 3-6, such as 3, 4, 5 or 6, and crosslinked with a crosslinking agent as defined above in this paragraph.

In some embodiments, the pharmaceutical composition of the present invention comprises an amine polyether polymer comprising at least one amine polyether compound or residue thereof, where the amine polyether compound is represented by Formula X where $R_5$ independently represents an H radical or an alkyl radical, q and r are 0 and p is 2, m independently represents an integer from 3-6, such as 3, 4, 5 or 6; and 2-6 wt. % crosslinking agent or residue thereof, such as 2 wt. %, 3 wt. %, 4 wt. %, 5 wt. % or 6 wt. % crosslinking agent, where the crosslinking agent is epichlorohydrin, poly(epichlorohydrin), 1,2-dibromoethane, tris(2-chloroethyl)amide or 1,4-butanediol diglycidyl ether. Another pharmaceutical composition embodiment of the present invention comprises an amine polyether polymer comprising at least one amine polyether compound or residue thereof, where the amine polyether compound is represented by Formula X where $R_5$ independently represents an H radical or an alkyl radical, q is 0 and r and p both are 2, m independently represents an integer from 3-6, such as 3, 4, 5 or 6, where the compound is crosslinked with a crosslinking agent as defined above in this paragraph. A further pharmaceutical composition embodiment of the present invention comprises an amine polyether polymer comprising at least one amine polyether compound or residue thereof, where the amine polyether compound is represented by Formula X where $R_5$ independently represents an H radical or an alkyl radical, q, r and p are each 2, m independently represents an integer from 3-6, such as 3, 4, 5 or 6, where the compound is crosslinked with a crosslinking agent as defined above in this paragraph.

In some embodiments, the invention is a compound or composition or method for removing an anion, such as organophosphate or phosphate, from the gastrointestinal tract of an animal by administering a therapeutically effective amount of an amide polymer that comprises an amide dendrimer having a core that is a residue of an amide polyol and a residue of one or more substituted or un-substituted α, β unsaturated nitriles, where the amide polyol comprises a residue of an organic polyacid or ester thereof and a residue of an amine polyol.

Another pharmaceutical composition of the present invention comprises an amide polymer that comprises an amide dendrimer or residue thereof having a core that is a residue of an amide polyol and a residue of one or more acrylonitriles, where the amide polyol is a residue of tartaric acid or other aldaric acid or an ester of tartaric acid or other aldaric acid, and a residue of tris(hydroxymethyl)aminomethane; where the dendrimer is crosslinked with 2-6 wt. % crosslinking agent or residue thereof, such as 2 wt. %, 3 wt. %, 4 wt. %, 5 wt. % or 6 wt. % crosslinking agent, where the crosslinking agent is epichlorohydrin, poly(epichlorohydrin), 1,2-dibromoethane, tris(2-chloroethyl)amide or 1,4-butanediol diglycidyl ether. Another pharmaceutical composition embodiment of the present invention comprises an amide polymer that comprises an amide dendrimer or residue thereof having a core that is a residue of an amide polyol and a residue of one or more acrylonitriles, where the amide polyol is a residue of methantetracarboxylic acid and tris(hydroxymethyl)aminomethane; and where the dendrimer is crosslinked with a crosslinking agent as defined above in this paragraph.

Another pharmaceutical composition of the present invention comprises a polymer network having a plurality of units represented by Formula VIII where n is from 3-6, the composition also having a plurality of units represented by Formula IX.

The polymers of some embodiments may be formed using a polymerization initiator. Generally, any initiator may be used including cationic and radical initiators. Some examples of suitable initiators that may be used include: the free radical peroxy and azo type compounds, such as azodiisobutyronitrile, azodiisovaleronitrile, dimethylazodiisobutyrate, 2,2'-azobis(isobutyronitrile), 2,2'-azobis(N,N'-dimethyleneisobutyramidine)dihydrochloride, 2,2'-azobis(2-amidinopropane)dihydrochloride, 2,2'-azobis(N,N'-dimethyleneisobutyramidine), 1,1'-azobis(1-cyclohexanecarbo-nitrile), 4,4'-azobis(4-cyanopentanoic acid), 2,2'-azobis(isobutyramide)dihydrate, 2,2'-azobis(2-methylpropane), 2,2'-azobis(2-methylbutyronitrile), VAZO 67, cyanopentanoic acid, the peroxy pivalates, dodecylbenzene peroxide, benzoyl peroxide, di-t-butyl hydroperoxide, t-butyl peracetate, acetyl peroxide, dicumyl peroxide, cumyl hydroperoxide, dimethyl bis(butylperoxy) hexane.

In some embodiments, any of the nitrogen atoms within the amide compounds or residues thereof or amine polyether compounds or residues thereof according to embodiments of the invention may optionally be quaternized to yield the corresponding positively charged tertiary nitrogen group, such as for example, an ammonium or substituted ammonium group. Any one or more of the nitrogen atoms in the amide compound or residue thereof or amine polyether compound or residue thereof may be quaternized and such quaternization, when present, is not limited to or required to include terminal amine nitrogen atoms. In some embodiments, this quaternization may result in additional network formation and may be the result of addition of crosslinking, linking or addition of amine reactive groups to the nitrogen. The ammonium groups may be associated with a pharmaceutically acceptable counterion.

In some embodiments, amide compounds, amide polymers, amine polyether compounds and amine polyether polymers of the invention may be partially or fully quaternized or partially or fully protonated, with a pharmaceutically acceptable counterion, which may be organic ions, inorganic ions, or a combination thereof. Examples of some suitable inorganic ions include halides (e.g., chloride, bromide or iodide) carbonates, bicarbonates, sulfates, bisulfates, hydroxides, nitrates, persulfates and sulfites. Examples of some suitable organic ions include acetates, ascorbates, benzoates, citrates, dihydrogen citrates, hydrogen citrates, oxalates, succinates, tartrates, taurocholates, glycocholates, and cholates. Preferred ions include chlorides and carbonates.

In some embodiments, amide compounds, amide polymers, amine polyether compounds and amine polyether polymers of the invention may be protonated such that the fraction of protonated nitrogen atoms is from 1 to 25%, preferably 3 to 25%, more preferably 5 to 15%.

In one embodiment, a pharmaceutically acceptable amide polymer or amine polyether polymer is an amide polymer or amine polyether polymer in partially or fully protonated form and comprises a carbonate anion. In one embodiment the pharmaceutically acceptable amide polymer or pharmaceutically acceptable amine polyether polymer is in partially or fully protonated form and comprises a mixture of carbonate and bicarbonate anions.

In some embodiments, compounds and polymers of the invention are characterized by their ability to bind compounds or ions. Preferably the compounds or polymers of the invention bind anions, more preferably they bind organophosphates, phosphate and/or oxalate, and most preferably they bind organophosphates or phosphate. For illustration, anion-binding amide polymers, anion binding amine polyether polymers and especially organophosphate or phosphate-binding amide polymers and organophosphate or phosphate-binding amine polyether polymers will be described; however, it is understood that this description applies equally, with appropriate modifications that will be apparent to those of skill in the art, to other ions, compounds and solutes. Amide polymers and amine polyether polymers may bind an ion, e.g., an anion when they associate with the ion, generally though not necessarily in a noncovalent manner, with sufficient association strength that at least a portion of the ion remains bound under the in vitro or in vivo conditions in which the polymer is used for sufficient time to effect a removal of the ion from solution or from the body. A target ion may be an ion to which the amide polymer or amine polyether polymer binds, and usually refers to the ion whose binding to the amide polymer or amine polyether polymer is thought to produce the therapeutic effect of the compound and may be an anion or a cation. A compound of the invention may have more than one target ion.

For example, some of the amide polymers and amine polyether polymers described herein exhibit organophosphate or phosphate binding properties. Phosphate binding capacity is a measure of the amount of phosphate ion a phosphate binder can bind in a given solution. For example, binding capacities of phosphate binders can be measured in vitro, e.g., in water or in saline solution, or in vivo, e.g., from phosphate urinary excretion, or ex vivo, for example using aspirate liquids, e.g., chyme obtained from lab animals, patients or volunteers. Measurements can be made in a solution containing only phosphate ion, or at least no other competing solutes that compete with phosphate ions for binding to the amide polymer or amine polyether polymer. In these cases, a non interfering buffer may be used. Alternatively, measurements can be made in the presence of other competing solutes, e.g., other ions or metabolites, that compete with phosphate ions (the target solute) for binding to the amide polymer or amine polyether polymer.

Ion binding capacity for an amide polymer or amine polyether polymer may be measured as indicated in the Test Methods. Some embodiments have a phosphate binding capacity which can be greater than about 0.2, 0.5, 1.0, 1.5, 2.0, 2.5, 3.0, 3.5, 4.0, 5.0, 6.0, 8.0, 10.0, 12, 14, 16, 18 or greater than about 20 mmol/g. In some embodiments, the in vitro phosphate binding capacity of amide polymers or amine polyether polymers of the invention for a target ion is greater than about 0.5 mmol/g, preferably greater than about 2.5 mmol/g, even more preferably greater than about 3 mmol/g, even more preferably greater than about 4 mmol/g, and yet even more preferably greater than about 6 mmol/g. In some embodiments, the phosphate binding capacity can range from about 0.2 mmol/g to about 20 mmol/g, such as about 0.5 mmol/g to about 10 mmol/g, preferably from about 2.5 mmol/g to about 8 mmol/g, and even more preferably from about 3 mmol/g to about 6 mmol/g. Phosphate binding may be measured according to the techniques described in the Test Methods section below.

In some embodiments, amide compounds, amide polymers, amine polyether compounds, amine polyether polymers and compositions of the invention may reduce urinary phosphorous of a patient in need thereof by 5-100%, such as 10-75%, 25-65%, or 45-60%. Some embodiments may reduce urinary phosphorous by greater than 10%, greater than 20%, greater than 30%, greater than 40%, greater than 45%, greater than 50% or greater than 60%. Reduction of urinary phosphorous may be measured according to the methods detailed in the Test Methods section below.

In some embodiments, amide polymers, amine polyether polymers and compositions of the invention may reduce blood phosphate of a patient in need thereof by 5-100%, such as 10-75%, 25-65%, or 45-60%. Some embodiments may reduce blood phosphate levels by greater than 10%, greater than 20%, greater than 30%, greater than 40%, greater than 45%, greater than 50% or greater than 60%.

When crosslinked, some embodiments of the amide compounds and amine polyether compounds of the invention form a gel in a solvent, such as in a simulated gastrointestinal medium or a physiologically acceptable medium.

One aspect of the invention is core-shell compositions comprising a polymeric core and shell. In some embodiments, the polymeric core comprises the amide polymers or amine polyether polymers described herein. The shell material can be chemically anchored to the core material or physically coated. In the former case, the shell can be grown on the core component through chemical means, for example by: chemical grafting of shell polymer to the core using living polymerization from active sites anchored onto the core polymer; interfacial reaction, i.e., a chemical reaction located at the core particle surface, such as interfacial polycondensation; and using block copolymers as suspending agents during the core particle synthesis.

In some embodiments, the interfacial reaction and use of block polymers are the techniques used when chemical methods are used. In the interfacial reaction pathway, typically, the periphery of the core particle is chemically modified by reacting small molecules or macromolecules on the core interface. For example, an amide containing ion-binding core particle or an amine polyether containing ion-binding core particle is reacted with a polymer containing amine reactive groups such as epoxy, isocyanate, activated esters, halide groups to form a crosslinked shell around the core.

In another embodiment, the shell is first prepared using interfacial polycondensation or solvent coacervation to produce capsules. The interior of the capsule is then filled up with core-forming precursors to build the core within the shell capsule.

In some embodiments, using the block copolymer approach, an amphiphilic block copolymer can be used as a suspending agent to form the core particle in an inverse or direct suspension particle forming process. When an inverse water-in-oil suspension process is used, then the block copolymer comprises a first block soluble in the continuous oil phase and another hydrophilic block contains functional groups that can react with the core polymer. When added to the aqueous phase, along with core-forming precursor, and the oil phase, the block copolymer locates to the water-in-oil interface and acts as a suspending agent. The hydrophilic block reacts with the core material, or co-reacts with the core-forming precursors. After the particles are isolated from the oil phase, the block copolymers form a thin shell covalently attached to the core surface. The chemical nature and length of the blocks can be varied to vary the permeation characteristics of the shell towards solutes of interest.

When the shell material is physically adsorbed on the core material, well known techniques of microencapsulation such as solvent coacervation, fluidized bed spray coater, or multi-emulsion processes can be used. One method of microencapsulation is the fluidized bed spray coater in the Wurster configuration. In yet another embodiment, the shell material is only acting temporarily by delaying the swelling of the core particle while in the mouth and esophagus, and optionally disintegrates in the stomach or duodenum. The shell is then selected in order to hinder the transport of water into the core particle, by creating a layer of high hydrophobicity and very low liquid water permeability.

In one embodiment the shell material carries negative charges while being in the milieu of use. Not being limited to one mechanism of action, it is thought that negatively charged shell material coated on anion-binding beads enhance the binding of small inorganic ions with a low charge density (such as phosphate) over competing ions with greater valency or size. Competing anions such as citrate, bile acids and fatty acids among others, may thus have a lesser relative affinity to the anion binding core possibly as a result of their limited permeability across the shell.

In some embodiments, shell materials are polymers carrying negative charges in the pH range typically found in the intestine. Examples include, but are not limited to, polymers that have pendant acid groups such as carboxylic, sulfonic, hydrosulfonic, sulfamic, phosphoric, hydrophosphoric, phosphonic, hydrophosphonic, phosphoramidic, phenolic, boronic and a combination thereof. The polymer can be protonated or unprotonated; in the latter case the acidic anion can be neutralized with pharmaceutically acceptable cations such as Na, K, Li, Ca, Mg, and $NH_4$.

In another embodiment the polyanion can be administered as a precursor that ultimately activates as a polyanion: for instance certain labile ester or anhydride forms of either polysulfonic or polycarboxylic acids are prone to hydrolysis in the acidic environment of the stomach and can convert to the active anions.

The shell polymers can be either linear, branched, hyperbranched, segmented (i.e. backbone polymer arranged in sequence of contiguous blocks of which at least one contains pendant acidic groups), comb-shaped, star-shaped or crosslinked in a network, fully and semi-interpenetrated network (IPN). The shell polymers are either random or blocky in composition and either covalently or physically attached to the core material. Examples of such shell polymers include, but are not limited to acrylic acid homopolymers or copolymers, methacrylic acid homopolymers or copolymers, and copolymers of methacrylate and methacrylic acid. Examples of such polymers are copolymers of methylmethacrylate and methacrylic acid and copolymers of ethylacrylate and methacrylic acid, sold under the tradename Eudragit (Rohm GmbH & Co. KG): examples of which include Eudragit L100-55 and Eudragit L100 (a methylmethacrylate-methacrylic acid (1:1) copolymer, Degussa/Rohm), Eudragit L30-D55, Eudragit S 100-55 and Eudragit FS 30D, Eudragit S 100 (a methylmethacrylate-methacrylic acid (2:1) copolymer), Eudragit LD-55 (an ethylacrylate-methacrylic acid (1:1) copolymer), copolymers of acrylates and methacrylates with quaternary ammonium groups, sold under the tradenames Eudragit RL and Eudragit RS, and a neutral ester dispersion without any functional groups, sold under the tradename Eudragit NE30-D.

Additional shell polymers include: poly(styrene sulfonate), Polycarbophil®; Polyacrylic acid(s); carboxymethyl cellulose, cellulose acetate phthalate, hydroxypropyl methylcellulose phthalate as sold under the tradename HP-50 and HP-55 (Shin-Etsu Chemical Co., Ltd.), cellulose acetate trimellitate, cellulose acetate, cellulose acetate butyrate, cellulose acetate propionate, ethyl cellulose, cellulose derivatives, such as hydroxypropylmethylcellulose, methylceluose, hydroxylethylcellulose, hydroxyethylmethylcellulose, hydroxylethylethylcelluose and hydroxypropylethylcellulose and cellulose derivatives such as cellulose ethers useful in film coating formulations, polyvinyl acetate phthalate, carrageenan, alginate, or poly(methacrylic acid) esters, acrylic/ maleic acid copolymers, styrene/maleic acid polymers, itaconic acid/acrylic copolymers, and fumaric/acrylic acid copolymers, polyvinyl acetal diethylaminoacetate, as sold under the tradename AEA (Sankyo Co., Ltd.), methylvinylether/maleic acid copolymers and shellac.

In some embodiments the shell polymers are selected amongst pharmaceutically acceptable polymers such as Eudragit L100-55 and Eudragit L100 (a methylmethacrylate-methacrylic acid (1:1) copolymer, Degussa/Rohm), Carbopol 934 (polyacrylic acid, Noveon), C-A-P NF (cellulose acetate phthalate—Eastman), Eastacryl (methacrylic acid esters—Eastman), Carrageenan and Alginate (FMC Biopolymer), Anycoat—P (Samsung Fine Chemicals—HPMC Phthalate), or Aqualon (carboxymethyl cellulose—Hercules), methylvinylether/maleic acid copolymers (Gantrez), and styrene/maleic acid (SMA).

The shell can be coated by a variety of methods. In one embodiment, the shell materials are added in the drug formulation step as an active excipient; for example, the shell material can be included in a solid formulation as a powder, which is physically blended with the organophosphate or phosphate-binding polymer and other excipients, optionally granulated, and compressed to form a tablet. Thus, in some embodiments, the shell material need not cover the core material in the drug product. For example, the acidic shell polymer may be added together with the anion binding core polymer formulated in the shape of a tablet, capsule, gel, liquid, etc, wafer, extrudates and the shell polymer can then dissolve and distribute itself uniformly as a shell coating around the core while the drug product equilibrates in the mouth, esophagus or ultimately in the site of action, i.e. the GI tract.

In some embodiments, the shell is a thin layer of shell polymer. The layer can be a molecular layer of polyanion on the core particle surface. The weight to core ratio can be between about 0.0001% to about 30%, preferably comprised between about 0.01% to about 5%, such as between about 0.1% to about 5%.

The shell polymers have a minimum molecular weight such that they do not freely permeate within the core pore volume nor elute from the core surface. In some embodiments, the molecular weight (Mw) of the shell acidic polymer is above about 1000 g/mole, such as above about 5000 g/mole, and or even above about 20,000 g/mole.

The anionic charge density of the shell material (as prevailing in the milieu of use) is may be between 0.5 mEq/gr to 22 mEq/gr, such as 2 mEq/gr to 15 mEq/gr. If a coating process is used to form the shell on the polymer particles as part of the manufacture of the dosage form, then procedures known from those skilled-in-the-art in the pharmaceutical industry are applicable. In one embodiment, the shell is formed in a fluidized bed coater (Wurster coater). In an alternate embodiment, the shell is formed through controlled precipitation or coascervation, wherein the polymer particles are suspended in a polymer solution, and the solvent properties are changed in such a way as to induce the polymer to precipitate onto or coat the polymer particles.

Suitable coating processes include the procedures typically used in the pharmaceutical industry. Typically, selection of the coating method is dictated by a number of parameters, that include, but are not limited to the form of the shell material (bulk, solution, emulsion, suspension, melt) as well as the shape and nature of the core material (spherical beads, irregular shaped, etc.), and the amount of shell deposited. In addition, the cores may be coated with one or more shells and may comprise multiple or alternating layers of shells.

The term "phosphate imbalance disorder" as used herein refers to conditions in which the level of phosphorus present in the body is abnormal. One example of a phosphate imbalance disorder includes hyperphosphatemia. The term "hyperphosphatemia" as used herein refers to a condition in which the element phosphorus is present in the body at an elevated level. Typically, a patient is often diagnosed with hyperphosphatemia if the blood phosphate level is, for example, above about 4.0 or 4.5 milligrams per deciliter of blood, for example above about 5.0 mg/dl, such as above about 5.5 mg/dl, for example above 6.0 mg/dl, and/or the patient has a severely impaired glomerular filtration rate such as, for example, less than about 20% of normal. The present invention may also be used to treat patients suffering from hyperphosphatemia in End Stage Renal Disease and who are also receiving dialysis treatment (e.g., hemodialysis or peritoneal dialysis).

Other diseases that can be treated with the methods, compounds, polymers, compositions, and kits of the present invention include hypocalcemia, hyperparathyroidism, depressed renal synthesis of calcitriol, tetany due to hypocalcemia, renal insufficiency, and ectopic calcification in soft tissues including calcifications in joints, lungs, kidney, conjuctiva, and myocardial tissues. Also, the present invention can be used to treat Chronic Kidney Disease (CKD), End Stage Renal Disease (ESRD) and dialysis patients, including prophylactic treatment of any of the above.

The amide polymers, amine polyether polymers and compositions described herein can be used as an adjunct to other therapies e.g. those employing dietary control of phosphorus intake, dialysis, inorganic metal salts and/or other polymer resins.

The compositions of the present invention are also useful in removing chloride, bicarbonate, oxalate, and bile acids from the gastrointestinal tract. Amide polymers and amine polyether polymers removing oxalate compounds or ions find use in the treatment of oxalate imbalance disorders, such as oxalosis or hyperoxaluria that increases the risk of kidney stone formation. Amide polymers and amine polyether polymers removing chloride compounds or ions find use in treating acidosis, heartburn, acid reflux disease, sour stomach or gastritis, for example. In some embodiments, the amide polymers, amine polyether polymers and compositions of the present invention are useful for removing fatty acids, bilirubin, and related compounds. Some embodiments may also bind and remove high molecular weight molecules like proteins, nucleic acids, vitamins or cell debris.

The present invention provides methods, pharmaceutical compositions, polymers, compounds and kits for the treatment of animals. The term "animal" or "animal subject" or "patient" as used herein includes humans as well as other mammals (e.g., in veterinary treatments, such as in the treatment of dogs or cats, or livestock animals such as pigs, goats, cows, horses, chickens and the like). One embodiment of the invention is a method of removing phosphorous-containing compounds such as organophosphates or phosphate from the gastrointestinal tract, such as the stomach, small intestine or large intestine of an animal by administering a therapeutically effective amount of at least one of the amide polymers or amine polyether polymers described herein.

The term "treating" and its grammatical equivalents as used herein includes achieving a therapeutic benefit and/or a prophylactic benefit. By therapeutic benefit is meant eradication, amelioration, or prevention of the underlying disorder being treated. For example, in a hyperphosphatemia patient, therapeutic benefit includes eradication or amelioration of the underlying hyperphosphatemia. Also, a therapeutic benefit is achieved with the eradication, amelioration, or prevention of one or more of the physiological symptoms associated with the underlying disorder such that an improvement is observed in the patient, notwithstanding that the patient may still be afflicted with the underlying disorder. For example, administration of amide polymers or amine polyether polymers, described herein, to a patient suffering from renal insufficiency and/or hyperphosphatemia provides therapeutic benefit not only when the patient's serum phosphate level is decreased, but also when an improvement is observed in the patient with respect to other disorders that accompany renal failure and/or hyperphosphatemia like ectopic calcification and renal osteodistrophy. For prophylactic benefit, for example, the amide polymers or amine polyether polymers may be administered to a patient at risk of developing hyperphosphatemia or to a patient reporting one or more of the physiological symptoms of hyperphosphatemia, even though a diagnosis of hyperphosphatemia may not have been made.

The compositions may also be used to control serum phosphate in subjects with elevated phosphate levels, for example, by changing the serum level of phosphate towards a normal or near normal level, for example, towards a level that is within 10% of the normal level of a healthy patient.

Other embodiments of the invention are directed towards pharmaceutical compositions comprising at least one of the amide polymers or a pharmaceutically acceptable salt of the amide polymer, or at least one of the amine polyether polymers or a pharmaceutically acceptable salt of the amine polyether polymer and one or more pharmaceutically acceptable excipients, diluents, or carriers and optionally additional therapeutic agents. The compounds and polymers may be lyophilized or dried under vacuum or oven before formulating. The compositions may include a mixture of one or more compounds or polymers according to the invention and may be administered to bind one or more target ions.

The excipients or carriers are "acceptable" in the sense of being compatible with the other ingredients of the formulation and not deleterious to the recipient thereof. The formulations can conveniently be presented in unit dosage form and can be prepared by any suitable method. The methods typically include the step of bringing into association the agent with the excipients or carriers such as by uniformly and intimately bringing into association the amide polymer or amine polyether polymer with the excipients or carriers and then, if necessary, dividing the product into unit dosages thereof.

The pharmaceutical compositions of the present invention include compositions wherein the amide compounds, amide polymers, amine polyether compounds and/or amine polyether polymers are present in a therapeutically effective amount, i.e., in an amount effective to achieve therapeutic and/or prophylactic benefit. The actual amount effective for a particular application will depend on the patient (e.g. age, weight) the condition being treated; and the route of administration.

The dosages of the amide polymers or amine polyether polymers in animals will depend on the disease being treated, the route of administration, and the physical characteristics of the animal being treated. Such dosage levels in some embodiments for either therapeutic and/or prophylactic uses may be from about 1 gm/day to about 30 gm/day, for example from about 2 gm/day to about 20 gm/day or from about 3 gm/day to about 7 gm/day. The dose of the amide polymers or amine polyether polymers described herein can be less than about 50 gm/day, less than about 40 gm/day, less than about 30 gm/day, less than about 20 gm/day, and less than about 10 gm/day.

Typically, the amide polymers or amine polyether polymers can be administered before or after a meal, or with a meal. As used herein, "before" or "after" a meal is typically within two hours, preferably within one hour, more preferably within thirty minutes, most preferably within ten minutes of commencing or finishing a meal, respectively.

Generally, it is preferred that the amide polymers or amine polyether polymers are administered along with meals. The amide polymers or amine polyether polymers may be administered one time a day, two times a day, or three times a day. Preferably the amide polymers or amine polyether polymers are administered once a day with the largest meal.

Preferably, the amide polymers or amine poly ether polymers may be used for therapeutic and/or prophylactic benefits and can be administered alone or in the form of a pharmaceutical composition. The pharmaceutical compositions comprise the amide polymers or amine polyether polymers, one or more pharmaceutically acceptable carriers, diluents or excipients, and optionally additional therapeutic agents. For example, the amide polymers or amine polyether polymers of the present invention may be co-administered with other active pharmaceutical agents depending on the condition being treated. Examples of pharmaceutical agents that may be co-administered include, but are not limited to:

Other phosphate sequestrants including pharmaceutically acceptable lanthanum, calcium, aluminum, magnesium and zinc compounds, such as acetates, carbonates, oxides, hydroxides, citrates, alginates, and ketoacids thereof.

Calcium compounds, including calcium carbonate, acetate (such as PhosLo® calcium acetate tablets), citrate, alginate, and ketoacids, have been utilized for phosphate binding.

Aluminium-based phosphate sequestrants, such as Amphojel® aluminium hydroxide gel, have also been used for treating hyperphosphatemia. These compounds complex with intestinal phosphate to form highly insoluble aluminium phosphate; the bound phosphate is unavailable for absorption by the patient.

The most commonly used lanthanide compound, lanthanum carbonate (Fosrenol®) behaves similarly to calcium carbonate.

Other phosphate sequestrants suitable for use in the present invention include pharmaceutically acceptable magnesium compounds. Various examples of pharmaceutically acceptable magnesium compounds are described in U.S. Provisional Application No. 60/734,593 filed Nov. 8, 2005, the entire teachings of which are incorporated herein by reference. Specific suitable examples include magnesium oxide, magnesium hydroxide, magnesium halides (e.g., magnesium fluoride, magnesium chloride, magnesium bromide and magnesium iodide), magnesium alkoxides (e.g., magnesium ethoxide and magnesium isopropoxide), magnesium carbonate, magnesium bicarbonate, magnesium formate, magnesium acetate, magnesium trisilicates, magnesium salts of organic acids, such as fumaric acid, maleic acid, acrylic acid, methacrylic acid, itaconic acid and styrenesulfonic acid, and a combination thereof.

Various examples of pharmaceutically acceptable zinc compounds are described in PCT Application No. PCT/US2005/047582 filed Dec. 29, 2005, the entire teachings of which are incorporated herein by reference. Specific suitable examples of pharmaceutically acceptable zinc compounds include zinc acetate, zinc bromide, zinc caprylate, zinc carbonate, zinc chloride, zinc citrate, zinc formate, zinc hexafluorosilicate, zinc iodate, zinc iodide, zinc iodide-starch, zinc lactate, zinc nitrate, zinc oleate, zinc oxalate, zinc oxide, calamide (zinc oxide with a small proportion of ferric oxide), zinc p-phenolsulfonate, zinc propionate, zinc salicylate, zinc silicate, zinc stearate, zinc sulfate, zinc sulfide, zinc tannate, zinc tartrate, zinc valerate and zinc ethylenebis (dithiocarbamate). Another example includes poly(zinc acrylate).

When referring to any of the above-mentioned phosphate sequestrants, it is to be understood that mixtures, polymorphs and solvates thereof are encompassed.

In some embodiments, a mixture of the phosphate sequestrants described above can be used in the invention in combination with pharmaceutically acceptable ferrous iron salts.

In other embodiments, the phosphate sequestrant used in combination with compounds of the present invention is not a pharmaceutically acceptable magnesium compound. In yet other embodiments, the phosphate sequestrant used in combination with the pharmaceutically acceptable amide compounds, amide polymers, amine polyether compounds and/or amine polyether polymers is not a pharmaceutically acceptable zinc compound.

The invention also includes methods and pharmaceutical compositions directed to a combination therapy of the amide polymers or amine polyether polymers in combination with a phosphate transport inhibitor or an alkaline phosphatase inhibitor. Alternatively, a mixture of the amide polymers or amine polyether polymers is employed together with a phosphate transport inhibitor or an alkaline phosphatase inhibitor.

Suitable examples of phosphate transport inhibitors can be found in co-pending U.S. Application Publication Nos. 2004/0019113 and 2004/0019020 and WO 2004/085448, the entire teachings of each of which are incorporated herein by reference.

A large variety of organic and inorganic molecules are inhibitors to alkaline phosphatase (ALP) (see, for example, U.S. Pat. No. 5,948,630, the entire teachings of which are incorporated herein by reference). Examples of alkaline phosphatase inhibitors include orthophosphate, arsenate, L-phenylalanine, L-homoarginine, tetramisole, levamisole, L-p-Bromotetramisole, 5,6-Dihydro-6-(2-naphthyl) imidazo-[2,1-b]thiazole (napthyl) and derivatives thereof. The preferred inhibitors include, but are not limited to, levamisole, bromotetramisole, and 5,6-Dihydro-6-(2-naphthyl)imidazo-[2,1-b]thiazole and derivatives thereof.

This co-administration can include simultaneous administration of the two agents in the same dosage form, simultaneous administration in separate dosage forms, and separate administration. For example, for the treatment of hyperphosphatemia, the amide polymers or amine polyether polymers may be co-administered with calcium salts which are used to treat hypocalcemia resulting from hyperphosphatemia.

The pharmaceutical compositions of the invention can be formulated as a tablet, sachet, slurry, food formulation, troche, capsule, elixir, suspension, syrup, wafer, chewing gum or lozenge.

Preferably, the amide polymers, amine polyether polymers or the pharmaceutical compositions comprising the amide polymers or amine polyether polymers is administered orally. Illustrative of suitable methods, vehicles, excipients and carriers are those described, for example, in Remington's Pharmaceutical Sciences, 19th ed., the contents of which is incorporated herein by reference.

Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Suitable techniques for preparing pharmaceutical compositions of the amide polymers and amine polyether polymers are well known in the art.

In some aspects of the invention, the amide polymer(s) or amine polyether polymer(s) provide mechanical and thermal properties that are usually performed by excipients, thus decreasing the amount of such excipients required for the formulation. In some embodiments the amide polymer or amine polyether polymer constitutes over about 30 wt. %, for example over about 40 wt. %, over about 50 wt. %, preferably over about 60 wt. %, over about 70 wt. %, more preferably over about 80 wt. %, over about 85 wt. % or over about 90 wt. % of the composition, the remainder comprising suitable excipient(s).

In some embodiments, the compressibility of the tablets is strongly dependent upon the degree of hydration (moisture content) of the amide polymer or amine polyether polymer. Preferably, the amide polymer or amine polyether polymer has a moisture content of about 5% by weight or greater, more preferably, the moisture content is from about 5% to about 9% by weight, and most preferably about 7% by weight. It is to be understood that in embodiments in which the amide polymer or amine polyether polymer is hydrated, the water of hydration is considered to be a component of the amide polymer or amine polyether polymer.

The tablet can further comprise one or more excipients, such as hardeners, glidants and lubricants, which are well known in the art. Suitable excipients include colloidal silicon dioxide, stearic acid, magnesium silicate, calcium silicate, sucrose, calcium stearate, glyceryl behenate, magnesium stearate, talc, zinc stearate and sodium stearylfumarate.

The tablet core of embodiments of the invention may be prepared by a method comprising the steps of: (1) hydrating or drying the amide polymer or amine polyether polymer to the desired moisture level; (2) blending the amide polymer or amine polyether polymer with any excipients; and (3) compressing the blend using conventional tableting technology.

In some embodiments, the invention relates to a stable, swallowable coated tablet, particularly a tablet comprising a hydrophilic core, such as a tablet comprising the amide polymer or amine polyether polymer, as described above. In one embodiment, the coating composition comprises a cellulose derivative and a plasticizing agent. The cellulose derivative is, preferably, hydroxypropylmethylcellulose (HPMC). The cellulose derivative can be present as an aqueous solution. Suitable hydroxypropylmethylcellulose solutions include those containing HPMC low viscosity and/or HPMC high viscosity. Additional suitable cellulose derivatives include cellulose ethers useful in film coating formulations. The plasticizing agent can be, for example, an acetylated monoglyceride such as diacetylated monoglyceride. The coating composition can further include a pigment selected to provide a tablet coating of the desired color. For example, to produce a white coating, a white pigment can be selected, such as titanium dioxide.

In one embodiment, the coated tablet of the invention can be prepared by a method comprising the step of contacting a tablet core of the invention, as described above, with a coating solution comprising a solvent, at least one coating agent dissolved or suspended in the solvent and, optionally, one or more plasticizing agents. Preferably, the solvent is an aqueous solvent, such as water or an aqueous buffer, or a mixed aqueous/organic solvent. Preferred coating agents include cellulose derivatives, such as hydroxypropylmethylcellulose. Typically, the tablet core is contacted with the coating solution until the weight of the tablet core has increased by an amount ranging from about 4% to about 6%, indicating the deposition of a suitable coating on the tablet core to form a coated tablet.

Other pharmaceutical excipients useful in the some compositions of the invention include a binder, such as microcrystalline cellulose, carbopol, providone and xanthan gum; a flavoring agent, such as mannitol, xylitol, maltodextrin, fructose, or sorbitol; a lubricant, such as vegetable based fatty acids; and, optionally, a disintegrant, such as croscarmellose sodium, gellan gum, low-substituted hydroxypropyl ether of cellulose, sodium starch glycolate. Such additives and other suitable ingredients are well-known in the art; see, e.g., Gennaro A R (ed), Remington's Pharmaceutical Sciences, 19th Edition.

In some embodiments the amide polymers or amine polyether polymers of the invention are provided as pharmaceutical compositions in the form of chewable tablets. In addition to the active ingredient, the following types of excipients are commonly used: a sweetening agent to provide the necessary palatability, plus a binder where the former is inadequate in providing sufficient tablet hardness; a lubricant to minimize frictional effects at the die wall and facilitate tablet ejection; and, in some formulations a small amount of a disintegrant is added to facilitate mastication. In general excipient levels in currently-available chewable tablets are on the order of 3-5 fold of active ingredient(s) whereas sweetening agents make up the bulk of the inactive ingredients. In some embodiments the invention provides a pharmaceutical composition formulated as a chewable tablet, comprising an amide polymer or amine polyether polymer described herein, a filler, and a lubricant. In some embodiments the invention provides a pharmaceutical composition formulated as a chewable tablet, comprising an amide polymer or amine polyether polymer described herein, a filler, and a lubricant, wherein the filler is chosen from the group consisting of sucrose, mannitol, xylitol, maltodextrin, fructose, and sorbitol, and wherein the lubricant is a magnesium fatty acid salt, such as magnesium stearate.

In one embodiment, the amide polymer or amine polyether polymer is pre-formulated with a high Tg/high melting point low molecular weight excipient such as mannitol, sorbose, sucrose in order to form a solid solution wherein the polymer and the excipient are intimately mixed. Methods of mixing such as extrusion, spray-drying, chill drying, lyophilization, or wet granulation are useful. Indication of the level of mixing is given by known physical methods such as differential scanning calorimetry or dynamic mechanical analysis.

In some embodiments the amide polymers or amine polyether polymers of the invention are provided as pharmaceutical compositions in the form of liquid formulations. In some embodiments the pharmaceutical composition contains polymer dispersed in a suitable liquid excipient. Suitable liquid excipients are known in the art; see, e.g., Remington's Pharmaceutical Sciences.

In some embodiments, the pharmaceutical compositions may be in the form of a powder formulation packaged as a sachet that may be mixed with water or other ingestible liquid and administered orally as a drink (solution or suspension). In order to ensure that such formulations provide acceptable properties to the patient such as mouth feel and taste, a pharmaceutically acceptable anionic stabilizer may be included in the formulation.

Examples of suitable anionic stabilizers include anionic polymers such as: an anionic polypeptide, an anionic polysaccharide, or a polymer of one or more anionic monomers such as polymers of mannuronic acid, guluronic acid, acrylic acid, methacrylic acid, glucuronic acid glutamic acid or a combination thereof, and pharmaceutically acceptable salts thereof. Other examples of anionic polymers include cellulose, such as carboxyalkyl cellulose or a pharmaceutically acceptable salt thereof. The anionic polymer may be a homopolymer or copolymer of two or more of the anionic monomers described above. Alternatively, the anionic copolymer may include one or more anionic monomers and one or more neutral comonomers such as olefinic anionic monomers such as vinyl alcohol, acrylamide, and vinyl formamide.

Examples of anionic polymers include alginates (e.g. sodium alginate, potassium alginate, calcium alginate, magnesium alginate, ammonium alginate, and esters of alginate), carboxymethyl cellulose, polylactic acid, polyglutamic acid, pectin, xanthan, carrageenan, furcellaran, gum Arabic, karaya gum, gum ghatti, gum carob, and gum tragacanth. Preferred anionic polymers are alginates and are preferably esterified alginates such as a C2-C5-diol ester of alginate or a C3-C5 triol ester of alginate. As used herein an "esterified alginate" means an alginic acid in which one or more of the carboxyl groups have of the alginic acid are esterified. The remainder of the carboxylic acid groups in the alginate are optionally neutralized (partially or completely) as pharmaceutically acceptable salts. For example, propylene glycol alginate is an ester of alginic acid in which some of the carboxyl groups are esterified with propylene glycol, and the remainder of the carboxylic acid groups are optionally neutralized with pharmaceutically acceptable salts. More preferably, the anionic polymer is ethylene glycol alginate, propylene glycol alginate or glycerol alginate, with propylene glycol alginate even more preferred.

All publications and patent applications mentioned in this specification are herein incorporated by reference to the same extent as if each individual publication or patent application was specifically and individually indicated to be incorporated by reference.

It will be apparent to one of ordinary skill in the art that many changes and modification can be made to the disclosures presented herein without departing from the spirit or scope of the appended claims.

EXAMPLES

Example 1

Synthesis of an Amide Polyol

To a three-necked flask equipped with a magnetic stir bar was added 9 g of dimethyl L-tartarate, 12.85 g of tris(hydroxymethyl)aminomethane and 28 ml of methanol and the resulting solution was stirred at 50° C. for 20 hours. The addition of heat was stopped, and the solution was self-cooled to 42° C. and then filtered and dried at 30° C. in a vacuum oven for 20 hours to give 11.3 g of a white solid.

Test Methods

Amide Polymer/Amine Polyether Polymer Urinary Phosphorous Reduction (In Vivo-Rats)

House male Sprague Dawley (SD) rats are used for the experiments. The rats are placed singly in wire-bottom cages, fed with Purina 5002 diet, and allowed to acclimate for at least 5 days prior to experimental use.

To establish baseline phosphorus excretion, the rats are placed in metabolic cages for 48 hours. Their urine is collected and its phosphorus content analyzed with a Hitachi analyzer to determine phosphorus excretion in mg/day. Any rats with outlying values are excluded; and the remainder of the rats are distributed into groups.

Purina 5002 is used as the standard diet. The amide polymer or amine polyether polymer being tested is mixed with Purina 5002 to result in a final concentration 0.25%, 0.35%, 0.5% and 1% by weight of the feed. Cellulose at 0.5% by weight is used as a negative control. Sevelamer is used as a positive control. In the event that a high-fat diet is used, rats are given feed comprising Purina 5002, 0.25%, 0.35%, 0.5% and 1% by weight of the feed of the polymer and 10% by weight of the feed of purified Olive oil, with the purified olive oil commercially available from Sigma. For each rat, 200 g of diet is prepared.

Each rat is weighed and placed on the standard diet. After 4 days the standard diet is replaced with the treatment or high fat diet, (or control diet for the control group). On days 5 and 6, urine samples from the rats at 24 hours (+/−30 minutes) is collected and analyzed. The test rats are again weighed, and any weight loss or gain is calculated. Any remaining food is also weighed to calculate the amount of food consumed per day. A change in phosphorus excretion relative to baseline and cellulose negative control may be calculated. Percentage reduction of urinary phosphorous is determined by the following equation:

% Reduction of Urinary Phosphorous=[(urinary phosphorous of negative control (mg/day)−urinary phosphorous of experimental(mg/day))/urinary phosphorous of negative control(mg/day)]×100.

In Vitro Phosphate Binding (mmol/g)

Two samples per polymer are weighed into plastic bottles after having adjusted the weight of the polymer for the loss on drying of each sample. A 10 mM phosphate buffer solution containing 10 mM $KH_2PO_4$, 100 mM N,N-bis[2-hydroxyethyl]-2-aminoethanesulfonic acid, 80 mM NaCl, 15 mM glycochenodeoxycholic acid (GCDC), and 15 mM oleic acid (pH adjusted to 7.0 with 1 N NaOH) is prepared and well mixed. Aliquots of the 10 mM phosphate buffer solution is transferred into each of the two sample bottles. The solutions are well mixed and then placed into an orbital shaker at 37° C. for 1 hour. The polymer is allowed to settle prior to removing a sample aliquot from each solution. The sample aliquot is filtered into a small vial using a disposable syringe and syringe filter. The filtered sample is diluted 1-to-10 with DI water. The shaking is continued for a further 4 hours (total of 5 hours) and the sampling procedure is repeated. Phosphate standards are prepared from a 10 mM phosphate standard stock solution and diluted appropriately to provide standards in the range of 0.3 to 1.0 mM. Both the standards and samples are analyzed by ion chromatography. A standard curve is set up and the unbound phosphate (mM) for each test solution is calculated. Bound phosphate is determined by the following equation:

Bound Phosphate (mmol/g)=[(10−Unbound $PO_4$)× Vol.×1000]/MassP;

wherein Vol.=volume of test solution (L); MassP=LOD adjusted mass of polymer (mg).

In-Process Swelling Ratio (mL/g)

The in-process swelling ratio (SR) is determined by the following equation:

SR=(weight of wet gel (g)−weight of dry polymer (g))/weight of dry polymer (g).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating hyperphosphatemia comprising administering to a patient in need thereof a therapeutically effective amount of a pharmaceutical composition comprising, a) an amide compound represented by the following Formula III:

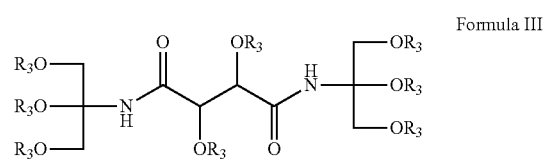

wherein $R_3$ is independently represented by the following Formula II:

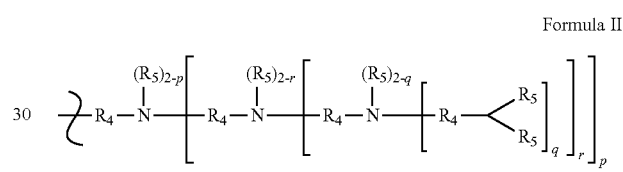

wherein p, q and r independently represent an integer from 0-2;

$R_4$ independently represents

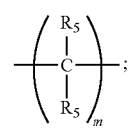

wherein m independently represents an integer from 1-20;

$R_5$ independently represents a hydrogen radical; a substituted or un-substituted alkyl radical; a substituted or un-substituted aryl radical; or $R_5$ and a neighboring $R_5$ together represent a link or links comprising a residue of a crosslinking agent, a substituted or un-substituted alicyclic radical, a substituted or un-substituted aromatic radical, or a substituted or un-substituted heterocyclic radical; or $R_5$ represents a link with another compound;

b) a crosslinking agent or residue thereof; and c) a pharmaceutically acceptable excipient.

2. A method of treating hyperphosphatemia comprising administering to a patient in need thereof a therapeutically effective amount of a pharmaceutical composition comprising a) an amide compound represented by the following Formula V:

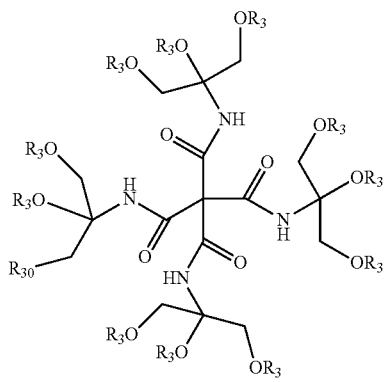

Formula V wherein
R₃ is independently represented by the following Formula II:

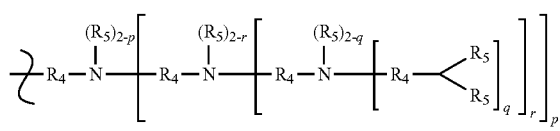

Formula II wherein
p, q and r independently represent an integer from 0-2;
R₄ independently represents

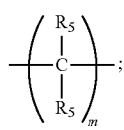

wherein
m independently represents an integer from 1-20;
R₅ independently represents a hydrogen radical; a substituted or un-substituted alkyl radical; a substituted or un-substituted aryl radical; or R₅ and a neighboring R₅ together represent a link or links comprising a residue of a crosslinking agent, a substituted or un-substituted alicyclic radical, a substituted or un-substituted aromatic radical, or a substituted or un-substituted heterocyclic radical; or R₅ represents a link with another compound;

b) a crosslinking agent or residue thereof; and
c) a pharmaceutically acceptable excipient.

3. A method of treating hyperphosphatemia comprising administering to a patient in need thereof a therapeutically effective amount of a pharmaceutical composition comprising a) an amide compound represented by the following Formula VI:

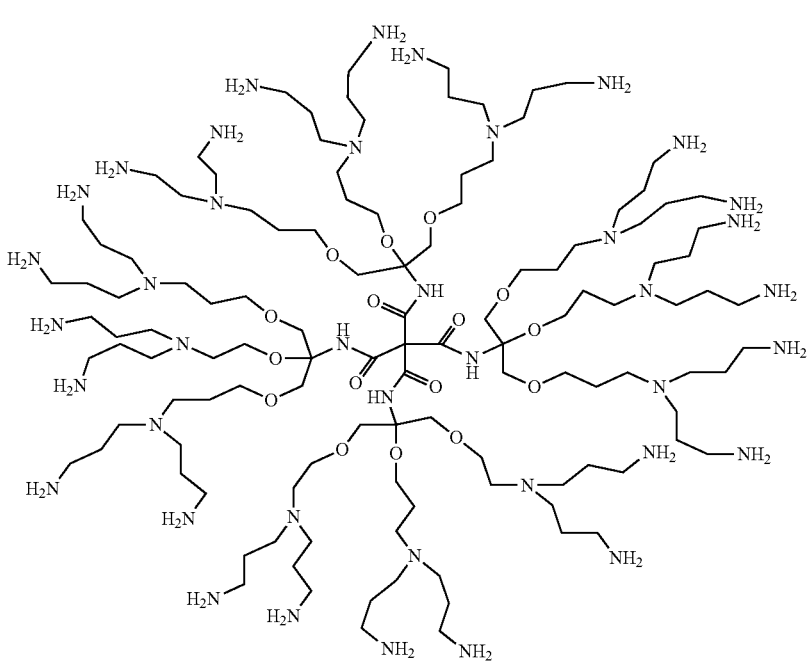

Formula VI b) a crosslinking agent or residue thereof; and
c) a pharmaceutically acceptable excipient.

\* \* \* \* \*